United States Patent
Lemke et al.

(10) Patent No.: US 11,492,608 B2
(45) Date of Patent: Nov. 8, 2022

(54) ARCHAEAL PYRROLYSYL TRNA SYNTHETASES FOR ORTHOGONAL USE

(71) Applicant: European Molecular Biology Laboratory, Heidelberg (DE)

(72) Inventors: Edward Lemke, Mannheim (DE); Ivana Nikic, Tübingen (DE); Gemma Estrada Girona, Heidelberg (DE); Christine Köhler, Forst (DE)

(73) Assignee: European Molecular Biology Laboratory, Heidelberg (DE)

( * ) Notice: Subject to any disclaimer, the term of this patent is extended or adjusted under 35 U.S.C. 154(b) by 526 days.

(21) Appl. No.: 16/340,476

(22) PCT Filed: Oct. 13, 2017

(86) PCT No.: PCT/EP2017/076140
§ 371 (c)(1),
(2) Date: Apr. 9, 2019

(87) PCT Pub. No.: WO2018/069481
PCT Pub. Date: Apr. 19, 2018

(65) Prior Publication Data
US 2020/0048625 A1 Feb. 13, 2020

(30) Foreign Application Priority Data
Oct. 14, 2016 (EP) .................................... 16194038

(51) Int. Cl.
C12N 9/00 (2006.01)
C12P 21/00 (2006.01)
(52) U.S. Cl.
CPC .............. C12N 9/93 (2013.01); C12P 21/00 (2013.01); C12Y 601/01026 (2013.01)
(58) Field of Classification Search
None
See application file for complete search history.

(56) References Cited

U.S. PATENT DOCUMENTS

| 8,242,088 B2 | 8/2012 | Joliot et al. |
| 9,085,514 B2 | 7/2015 | Lemke et al. |
| 2016/0340297 A1 | 11/2016 | Lemke et al. |

FOREIGN PATENT DOCUMENTS

| WO | 2012038706 A1 | 3/2012 |
| WO | 2012104422 A1 | 8/2012 |
| WO | 2015107064 A1 | 7/2015 |

OTHER PUBLICATIONS

Chin, J , et al., "Addition of p-Azido-L-phenylalanine to the Genetic Code of Escherichia coli", J AM Chem Soc 124, 9026-9027 (2002).
Chin, J , et al., "An Expanded Eukaryotic Genetic Code", Science vol. 301, 964-967 (2003).
Chin, J , "Expanding and Reprogramming the Genetic Code of Cells and Animals", Annu Rev Biochem 83, 379-408 (2014).
Kobayashi, N , et al., "Nuclear Translocation Peptides as Antibiotics", Antimicrobial Agents and Chemotherapy 50 (3), 1118-1119 (2006).
Lemke, E , "The Exploding Genetic Code", ChemBioChem 15, 1691-1694 (2014).
Nguyen, D , et al., "Genetic Encoding and Labeling of Aliphatic Azides and Alkynes in Recombinant Proteins via a Pyrrolysyl-tRNA Synthetase/tRNA CUA Pair and Click Chemistry", J Am Chem Soc 131, 8720-8721 (2009).
Nikic, I, et al., "Genetic code expansion enabled site-specific dual-color protein labeling: superresolution microscopy and beyond", Current Opinion in Chemical Biology 28, 164-173 (2015).
Nikic, I , et al., "Minimal Tags for Rapid Dual-Color Live-Cell Labeling and Super-Resolution Microscopy", Angew Chem Int Ed 53, 2245-2249 (2014).
Nikic, I , et al., "Verbesserte Erweiterung des eukaryotischen genetischen Codes fur seitenspezifische, nochauflosende Click-PAINT-Mikroskopie", Angew Chem 128 (52), 16406-16410 (2016). [English Abstract].
Patent Cooperation Treaty , International Searching Authority, Search Report and Written Opinion for PCT/EP2017/076140, 12 pages, Jan. 3, 2018.
Plass, T , et al., "Amino Acids for Diels-Alder Reactions in Living Cells", Angew Chem Int Ed 51, 4166-4170 (2012).
Uttamapinant, C , et al., "Genetic Code Expansion Enables Live-Cell and Super-Resolution Imaging of Site-Specifically Labeled Cellular Proteins", J Am Chem Soc 137, 4602-4605 (2015).
Yanagisawa, T , et al., "Multistep Engineering of Pyrrolysyl-tRNA Synthetase to Genetically Encode Nε-(p-Azidobenzyloxycarbonyl) lysine for Site-Specific Protein Modification", Chemistry and Biology 15, 1187-1197 (2008).

*Primary Examiner* — Kagnew H Gebreyesus
(74) *Attorney, Agent, or Firm* — Viksnins Harris Padys Malen LLP

(57) ABSTRACT

The invention relates to archaeal pyrrolysyl tRNA synthetases lacking a nuclear localization signal and/or comprising a nuclear export signal. The invention also relates to polynucleotides encoding said pyrrolysyl tRNA synthetases, eukaryotic cells comprising said polynucleotide and tRNA acylated by the pyrrolysyl tRNA synthetase or a polynucleotide encoding such tRNA, methods utilizing said cells for preparing polypeptides comprising unnatural amino acid residues, and kits useful in said methods.

5 Claims, 10 Drawing Sheets
Specification includes a Sequence Listing.

ARCHAEAL PYRROLYSYL TRNA SYNTHETASES FOR ORTHOGONAL USE

FIELD OF THE INVENTION

The invention relates to archaeal pyrrolysyl tRNA synthetases lacking a nuclear localization signal and/or comprising a nuclear export signal, polynucleotides encoding said pyrrolysyl tRNA synthetase, eukaryotic cells comprising said polynucleotide and tRNA acylated by the pyrrolysyl tRNA synthetase or a polynucleotide encoding such tRNA, methods utilizing said cells for preparing polypeptides comprising unnatural amino acid residues, and kits useful in said methods.

BACKGROUND OF THE INVENTION

The ability to visualize biomolecules within living specimens by engineered fluorescence tags or other labels which allow imaging has become a major tool in modern biotechnology, cell biology, and life sciences. A major challenge common to these label-based imaging techniques is to genetically encode a labeling site that is, ideally, as small as possible.

Genetic code expansion resulting in translational modification of proteins by direct genetic encoding of unnatural amino acids, in particular using stop codon suppression, by means of a tRNA/aminoacyl tRNA synthetase (tRNA/RS) pair that is orthogonal to the host machinery offers exquisite specificity, freedom of placement within the target protein and minimal structural change. This approach has meanwhile been used to genetically encode several unnatural amino acid residues of interest. For instance, engineered *Methanococcus jannaschii* tRNA/tyrosyl tRNA synthetase, *E. coli* tRNA/leucyl tRNA synthetase as well as *Methanosarcina mazei* and *M. barkeri* tRNA/pyrrolysyl tRNA synthetase pairs have been used to genetically encode a variety of functionalities in polypeptides (Chin et al., J Am Chem Soc 124:9026, 2002; Chin et al., Science 301:964, 2003; Nguyen et al, J Am Chem Soc 131:8720, 2009; Yanagisawa et al., Chem Biol 15:1187, 2008). Up to now, more than 200 different unnatural amino acids (for review see e.g. Liu et al., Annu Rev Biochem 83:379-408, 2010; Lemke, ChemBioChem 15:1691-1694, 2014) have been incorporated with residue precision.

The present inventors and others have recently shown that unnatural amino acids containing strained alkynyl or strained alkenyl groups can be encoded in living mammalian cells in response to the amber codon by means of the tRNA/pyrrolysyl tRNA synthetase pair originating from *Methanosarcina mazei* (Plass et al., Angew Chem Int Ed Engl 51(17):4166-4170, 2012; WO 2012/104422). Polypeptides which comprise unnatural amino acid residues carrying reactive groups such as strained alkynyl, strained alkenyl or norbornenyl groups can be used for ultrafast and bioorthogonal click reactions, such as strain-promoted inverse-electron-demand Diels-Alder cycloaddition (SPIEDAC) and strain promoted alkyne-azide cycloaddition (SPAAC), with tetrazines or azides, respectively. Dyes functionalized with tetrazines have previously been used in such click reactions to label either surface proteins or cytoskeletal proteins in mammalian cells for very high resolution imaging methods (Nikic et al., Angew Chem Int Ed Engl 53(8): 2245-2249, 2014; WO 2015/107064; Uttamapinant et al., J Am Chem Soc 137(14):4602-4605, 2015).

Among the biggest issues of genetic code expansion in general, and thus in particular for high resolution imaging methods based thereon, is the competition of stop codon suppression with the host's internal translation termination machinery which leads to limited efficiency in labeling less-abundant proteins inside cells. Many approaches have been explored to address this key issue of genetic code expansion in eukaryotes, including promoter engineering, better evolution of the RSs, release-factor engineering and multi-chaining of tRNAs, to just name a few (for review see, e.g., Chin et al., Annu Rev Biochem 83:379-408, 2014).

Despite these efforts, there is still a high demand for strategies which improve efficiency of genetic code expansion in eukaryotic cells (and thus the amount of target polypeptide comprising unnatural amino acid residues that is expressed by the cell and can be used for labeling and imaging purposes) so as to allow for efficient labeling, even of polypeptides of low abundance, and the use of super-resolution microscopy (SRM). It was therefore an object of the present invention to address this challenge.

SUMMARY OF THE INVENTION

The inventors identified a sequence within archaeal pyrrolysyl tRNA synthetases that can act as a nuclear localization signal in eukaryotic cells. The inventors showed that the efficiency of genetic code expansion based on archaeal pyrrolysyl tRNA synthetase can be increased if the amino acid sequence of the synthetase is modified such that it is not directed to the nucleus. To this end, the nuclear localization signal can be removed from the synthetase or can be overridden by introducing a suitable nuclear export signal.

The inventors assume that mislocation of archaeal pyrrolysyl tRNA synthetases expressed within eukaryotic cells to the nucleus limits the efficiency of genetic code expansion based on such synthetases because it limits the amount of synthetase available in the cytoplasm where translation takes place. It is believed that during translation an unnatural amino acid is more likely to be incorporated into a growing polypeptide chain if, in the cytoplasm of the cell, in particular at the ribosomes, there is a high concentration of archaeal pyrrolysyl tRNA synthetase and a high concentration of the tRNA that is acylated by the synthetase with the unnatural amino acid.

Accordingly, the present invention relates to an archaeal pyrrolysyl tRNA synthetase (PylRS) that lacks a nuclear localization signal (NLS) and/or comprises a nuclear export signal (NES). The present invention also provides polynucleotides encoding a PylRS of the invention.

The present invention further provides a combination of polynucleotides comprising at least one polynucleotide encoding a PylRS of the invention and at least one polynucleotide encoding a tRNA$^{Pyl}$, wherein the tRNA$^{Pyl}$ is a tRNA that can be acylated by said PylRS.

The present invention also relates to a eukaryotic cell, preferably a mammalian cell, comprising (i) a polynucleotide sequence that encodes a PylRS of the invention and (ii) a tRNA$^{Pyl}$ that can be acylated by said PylRS or a polynucleotide sequence that encodes such tRNA$^{Pyl}$. The polynucleotide sequence encoding the tRNA$^{Pyl}$ may be located on the polynucleotide encoding the PylRS or on a separate polynucleotide. Expediently, the eukaryotic cell is capable of expressing the PylRS and, if applicable, the tRNA$^{Pyl}$.

The present invention also relates to a method for preparing a target polypeptide comprising one or more than one unnatural amino acid (UAA) residue, wherein the method comprises:

(a) providing a eukaryotic cell of the present invention comprising:
  (i) a PylRS of the invention,
  (ii) a tRNA (tRNA$^{Pyl}$),
  (iii) an UAA or a salt thereof, and
  (iv) a polynucleotide encoding the target polypeptide, wherein any position of the target polypeptide occupied by an UAA residue is encoded by a codon that is the reverse complement of the anticodon comprised by the tRNA$^{Pyl}$; and
  wherein the PylRS (i) is capable of acylating the tRNA$^{Pyl}$ (ii) with the UAA or the salt of (iii); and
(b) allowing for translation of the polynucleotide (iv) by the eukaryotic cell, thereby producing the target polypeptide.

The present invention also relates to a method for preparing a polypeptide conjugate comprising:
(a) preparing a target polypeptide comprising one or more than one UAA residue using a method of the present invention; and
(b) reacting the target polypeptide with one or more than one conjugation partner molecule such that the conjugation partner molecules bind covalently to the UAA residue(s) of the target polypeptide.

The present invention further relates to kits comprising a polynucleotide or combination of polynucleotides or eukaryotic cell of the present invention. According to one embodiment, the invention provides a kit comprising at least one UAA, or a salt thereof, and a polynucleotide encoding a PylRS of the invention. According to another embodiment, the invention provides a kit comprising at least one UAA, or a salt thereof, and a eukaryotic cell of the present invention. The kit may further comprise a tRNA$^{Pyl}$ that can be acylated by the PylRS, or a polynucleotide sequence encoding such tRNA$^{Pyl}$. The tRNA$^{Pyl}$-encoding polynucleotide sequence can be located on the polynucleotide encoding the PylRS of the invention or on a separate polynucleotide. The PylRS of the invention is capable of acylating the tRNA$^{Pyl}$ with the UAA, or salt thereof. Such kits are useful for expressing a target polypeptide having one or more than one UAA residue within a eukaryotic cell. Such kits may thus further comprise instructions for expressing a target polypeptide having one or more than one UAA residue within a eukaryotic cell, e.g. using a method of the present invention.

BRIEF DESCRIPTION OF THE FIGURES

FIG. 6 shows the accumulated data of a titration over different DNA concentrations described in example 3 below.

FIG. 8(a) shows a schematic representation of the Click-PAINT method, wherein a polynucleotide sequence encoding a polypeptide of interest having an amino acid residue encoded an amber codon ("POI(TAG)"), is expressed in eukaryotic (e.g., mammalian) cells co-transfected with the amber suppression pair tRNA$^{Pyl}$/NES-PylRS$^{AF}$ in the presence of an UAA comprising a trans-cyclooctenyl group (e.g. UAA 2); the expressed polypeptide of interest (POI) comprising the UAA incorporated at the amber encoded position is subjected to a two-step labeling reaction, wherein a tetrazine-coupled docking DNA strand is chemically coupled to the UAA-derived amino acid residue of the POI by a SPIEDAC reaction and second, a complementary imager strand conjugated with a dye, is added to the cells.

DETAILED DESCRIPTION OF THE INVENTION

Figure 1:
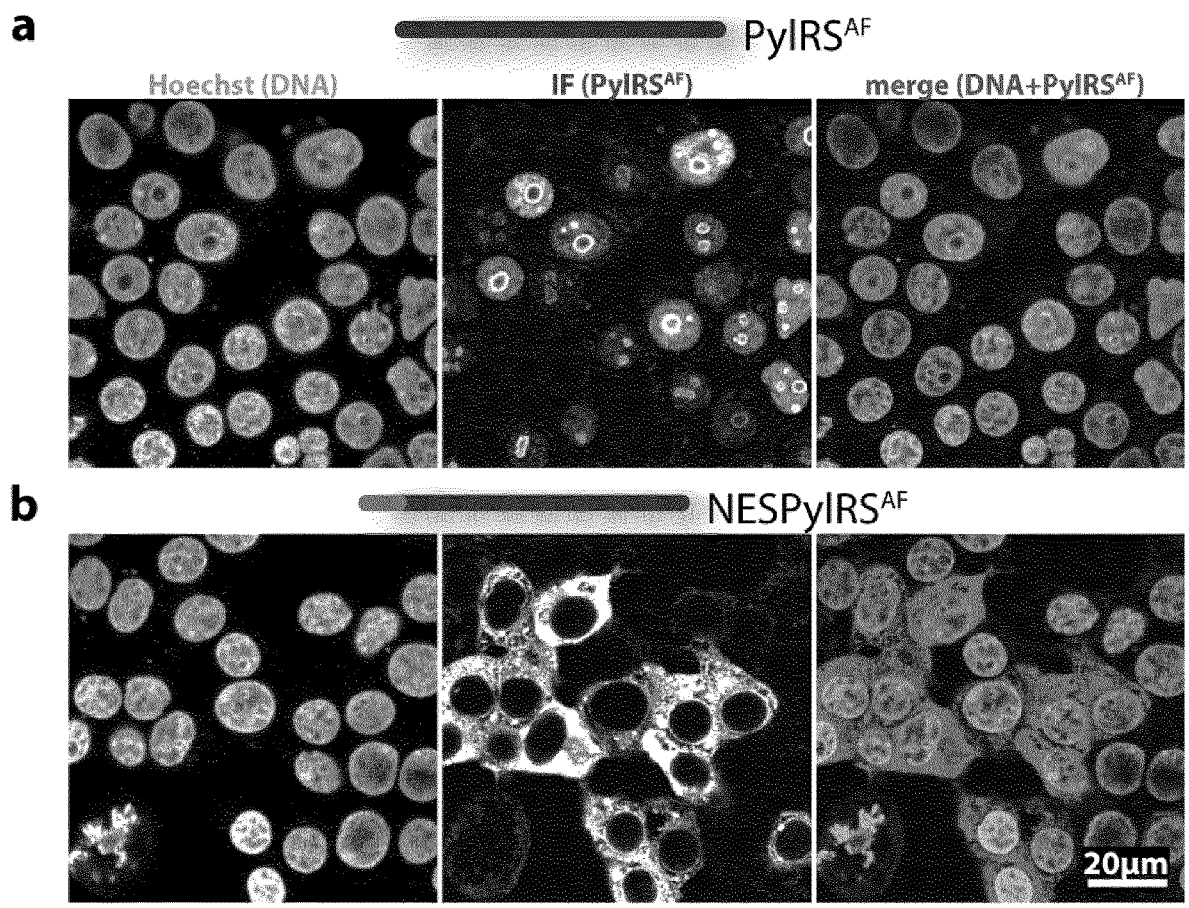
FIG. 1 shows the structures of UAAs 1 and 2; and HEK293T cells transfected with either tRNA$^{Pyl}$/PylRS$^{AF}$ (a) or tRNA$^{Pyl}$/NES-PylRS$^{AF}$ (b), left panel: stained with Hoechst 33342, center panel: immunostained with polyclonal rat anti-PylRS antibody+goat anti-rat IgG(H+L) Alexa Fluor 594 conjugate, right panel: merge.
Figure 1:
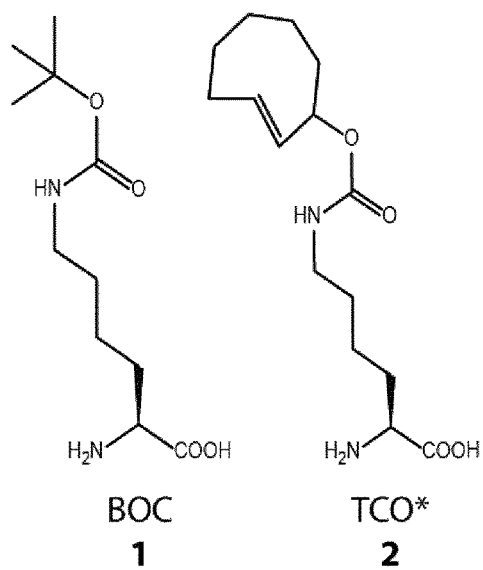
Figure 2:
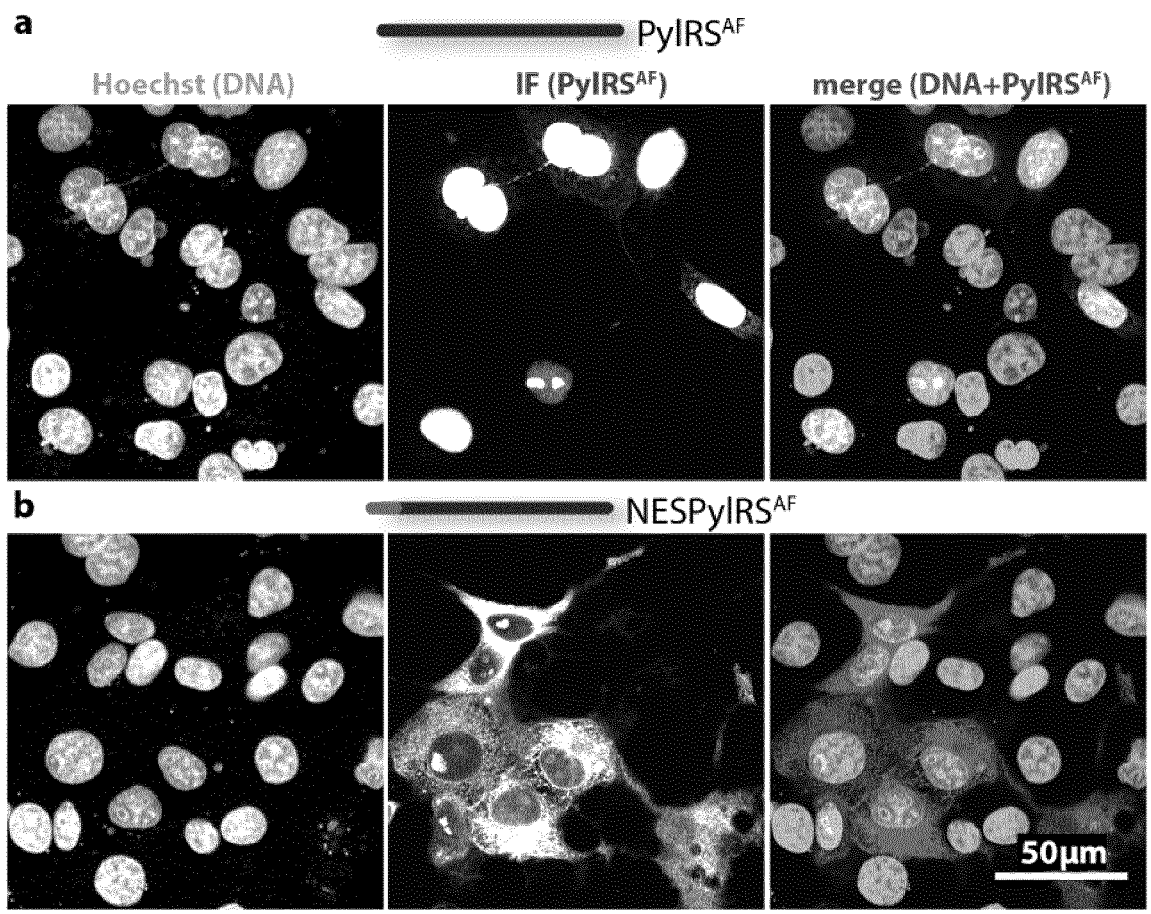
FIG. 2 shows COS-7 cells transfected with either tRNA$^{Pyl}$/PylRS$^{AF}$ (a) or tRNA$^{Pyl}$/NES-PylRS$^{AF}$ (b), left panel: stained with Hoechst 33342, center panel: immunostained with polyclonal rat anti-PylRS antibody+goat anti-rat IgG(H+L) Alexa Fluor 594 conjugate, right panel: merge.
Figure 3:
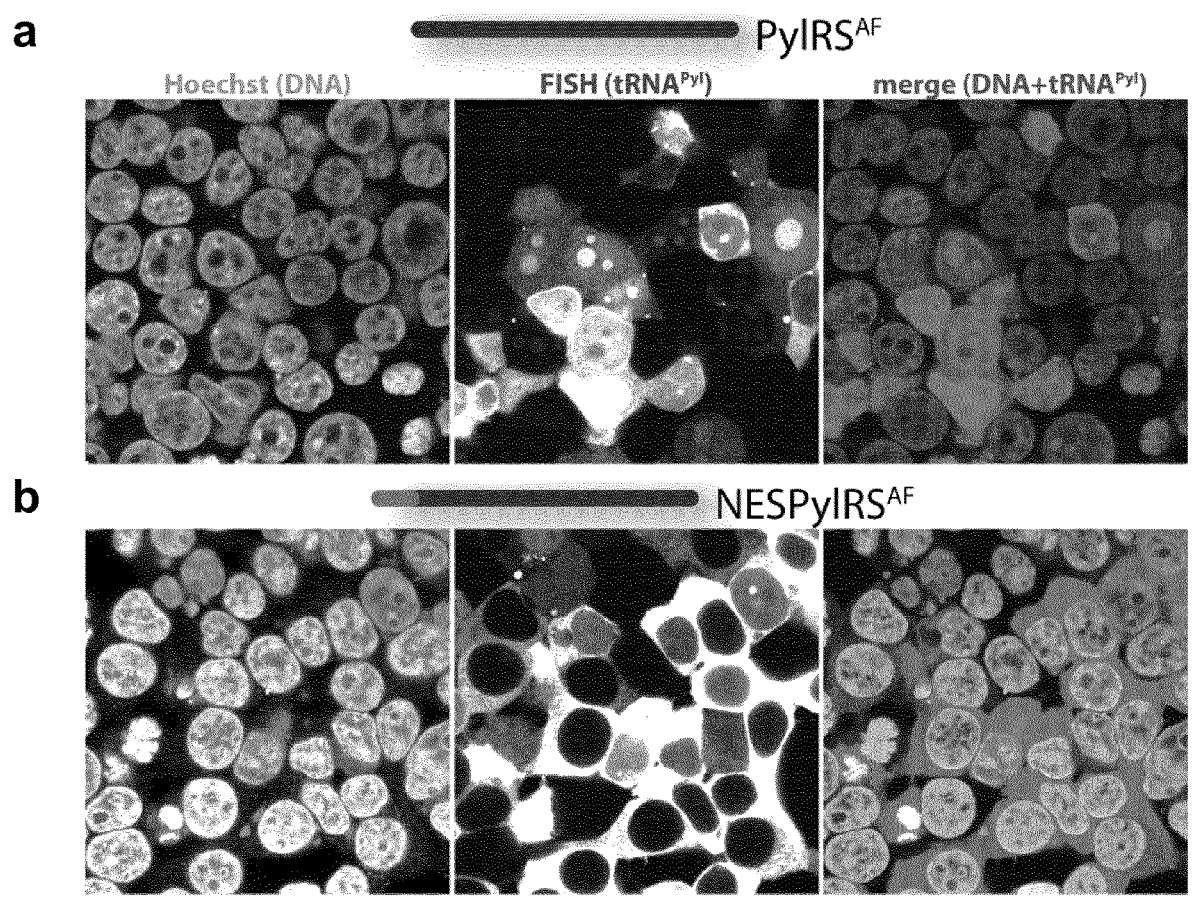
FIG. 3 shows HEK293T cells transfected with either tRNA$^{Pyl}$/PylRS$^{AF}$ (a) or tRNA$^{Pyl}$/NES-PylRS$^{AF}$ (b), left panel: stained with Hoechst 33342, center panel: fluorescence in situ hybridization (FISH) with tRNA$^{Pyl}$, right panel: merge.
Figure 4:
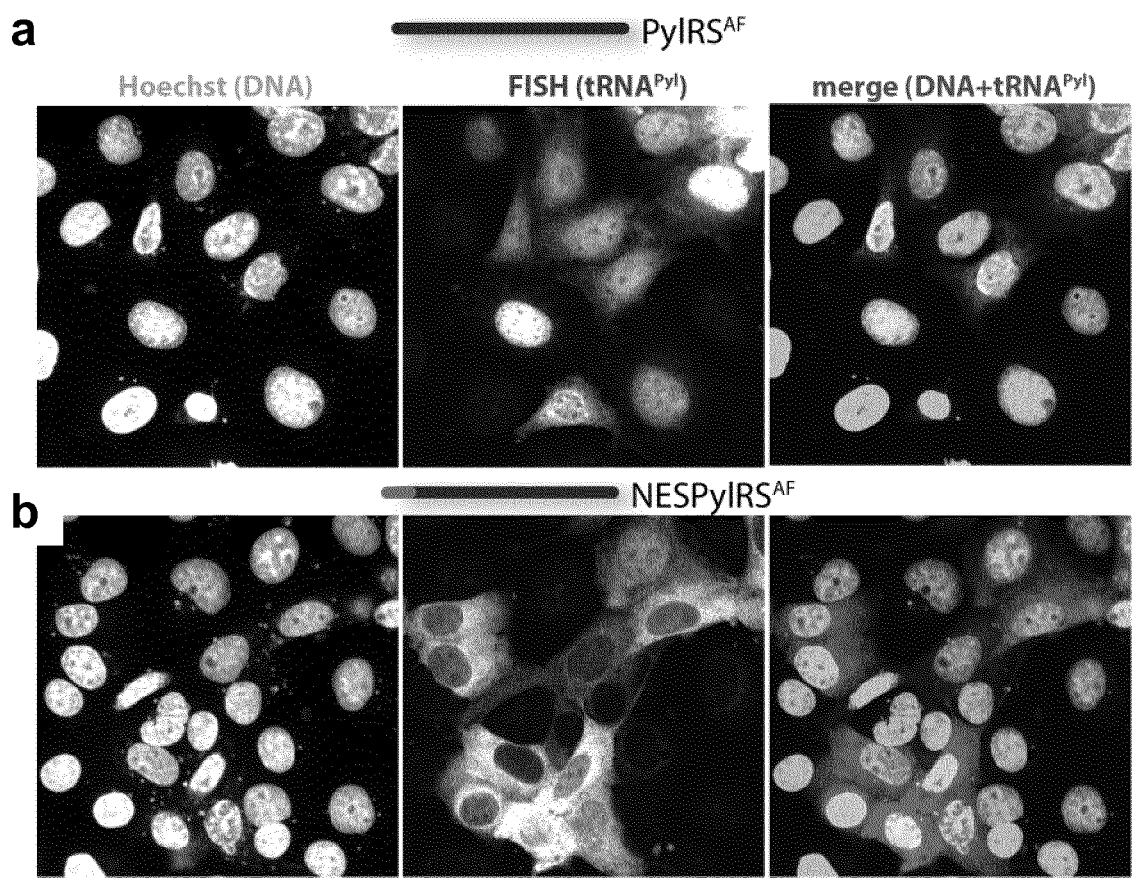
FIG. 4 shows COS-7 cells transfected with either tRNA$^{Pyl}$/PylRS$^{AF}$ (a) or tRNA$^{Pyl}$/NES-PylRS$^{AF}$ (b), left panel: stained with Hoechst 33342, center panel: fluorescence in situ hybridization (FISH) with tRNA$^{Pyl}$, right panel: merge.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular.

The present invention provides an archaeal PylRS that (a) lacks an NLS, or (b) comprises a NES, or (c) both of (a) and (b).

Pyrrolysyl tRNA synthetase (PylRS) is an aminoacyl tRNA synthetase (RS). RSs are enzymes capable of acylating a tRNA with an amino acid or amino acid analog. Expediently, the PylRS of the invention is enzymatically active, i.e. is capable of acylating a tRNA (tRNA$^{Pyl}$) with a certain amino acid or amino acid analog, preferably with an UAA or salt thereof.

The term "archaeal pyrrolysyl tRNA synthetase" (abbreviated as "archaeal PylRS") as used herein refers to a PylRS, wherein at least a segment of the PylRS amino acid sequence, or the entire PylRS amino acid sequence, has at least 60%, at least 70%, at least 80%, at least 90%, at least 95%, at last 99%, or 100% sequence identity to the amino acid sequence of a naturally occurring PylRS from an archaeon, or to the amino acid sequence of an enzymatically active fragment of such naturally occurring PylRS.

In particular embodiments of the invention, the archaeon is a *Methanosarcina* species, for example *M. mazei* or *M. barkeri*. According to a preferred embodiment of the invention, the archaeon is *M. mazei*. According to a further preferred embodiment of the invention, the archaeon is *M. barkeri*.

The PylRS of the present invention may comprise a wildtype or mutant archaeal PylRS, or an enzymatically active fragment thereof.

Mutant archaeal PylRSs differ from the corresponding wildtype PylRSs in comprising additions, substitutions and/or deletions of one or more than one amino acid residue. Preferably, these are modifications which improve PylRS stability, alter PylRS substrate specificity and/or enhance PylRS enzymatic activity. For example, the mutant archaeal PylRS is a mutant as described in Yanagisawa et al., Chem Biol 2008, 15:1187, or EP2192185.

According to a particular embodiment, the PylRS of the invention comprises *M. mazei* wildtype PylRS, or an enzymatically active fragment thereof. The amino acid sequence of wildtype *M. mazei* PylRS is set forth in SEQ ID NO:1.

SEQ ID NO: 1

| | |
|---|---|
| MDKKPLNTLISATGLWMSRTGTIHKIKHHEVSRSKIYIEMACGDHLVVNNSRSSRTARAL | 60 |
| RHHKYRKTCKRCRVSDEDLNKFLTKANEDQTSVKVKVVSAPTRTKKAMPKSVARAPKPLE | 120 |
| NTEAAQAQPSGSKFSPAIPVSTQESVSVPASVSTSISSISTGATASALVKGNTNPITSMS | 180 |
| APVQASAPALTKSQTDRLEVLLNPKDEISLNSGKPFRELESELLSRRKKDLQQIYAEERE | 240 |
| NYLGKLEREITRFFVDRGFLEIKSPILIPLEYIERMGIDNDTELSKQIFRVDKNFCLRPM | 300 |
| LAPNLYNYLRKLDRALPDPIKIFEIGPCYRKESDGKEHLEEFTMLNFCQMGSGCTRENLE | 360 |
| SIITDFLNHLGIDFKIVGDSCMVYGDTLDVMHGDLELSSAVVGPIPLDREWGIDKPWIGA | 420 |
| GFGLERLLKVKHDFKNIKRAARSESYYNGISTNL | 454 |

According to another particular embodiment, the PylRS of the invention comprises a mutant *M. mazei* PylRS, or an enzymatically active fragment thereof. Said mutant *M. mazei* PylRS comprises one or more than one amino acid alteration (independently selected from substitutions, additions and deletions) relative to the corresponding wildtype *M. mazei* PylRS. According to specific embodiments, such amino acid alterations are selected from amino acid substitutions Y306A and Y384F. For example, the PylRS of the invention comprises mazei PylRS$^{AF}$, or an enzymatically active fragment thereof. The amino acid sequence of *M. mazei* PylRS$^{AF}$ is set forth in SEQ ID NO:2.

```
                                                              SEQ ID NO: 2
MDKKPLNTLISATGLWMSRTGTIHKIKHHEVSRSKIYIEMACGDHLVVNNSRSSRTARAL    60

RHHKYRKTCKRCRVSDEDLNKFLTKANEDQTSVKVKVVSAPTRTKKAMPKSVARAPKPLE   120

NTEAAQAQPSGSKFSPAIPVSTQESVSVPASVSTSISSISTGATASALVKGNTNPITSMS   180

APVQASAPALTKSQTDRLEVLLNPKDEISLNSGKPFRELESELLSRRKKDLQQIYAEERE   240

NYLGKLEREITRFFVDRGFLEIKSPILIPLEYIERMGIDNDTELSKQIFRVDKNFCLRPM   300

LAPNLANYLRKLDRALPDPIKIFEIGPCYRKESDGKEHLEEFTMLNFCQMGSGCTRENLE   360

SIITDFLNHLGIDFKIVGDSCMVFGDTLDVMHGDLELSSAVVGPIPLDREWGIDKPWIGA   420

GFGLERLLKVKHDFKNIKRAARSESYYNGISTNL                             454
```

According to a further particular embodiment, the PylRS of the invention comprises *M. barkeri* wildtype PylRS, or an enzymatically active fragment thereof. The amino acid sequence of wildtype *M. barkeri* PylRS is set forth in SEQ ID NO:3.

```
                                                              SEQ ID NO: 3
MDKKPLDVLISATGLWMSRTGILHKIKHHEVSRSKIYIEMACGDHLVVNNSRSCRTARAF    60

RHHKYRKICKRCRVSDEDINNFLIRSTESKNSVKVRVVSAPKVKKAMPKSVSRAPKPLEN   120

SVSAKASINTSRSVPSPAKSTPNSSVPASAPAPSLIRSQLDRVEALLSPEDKISLNMAKP   180

FRELEPELVIRRKNDFQRLYINDREDYLGKLERDITKFFVDRGFLEIKSPILIPAEYVER   240

MGINNDTELSKQIFRVDKNLCLRPMLAPTLYNYLRKLDRILPGPIKIFEVGPCYRKESDG   300

KEHLEEFTMVNFCQMGSGCTRENLEALIKEFLDYLEIDFEIVGDSCMVYGDILDIMHGDL   360

ELSSAVVGPVSLDREWGIDKPWIGAGFGLERLLKVMHGFKNIKRASRSESYYNGISTNL    419
```

The term "nuclear export signal" (abbreviated as "NES") refers to an amino acid sequence which can direct a polypeptide containing it (such as a NES-containing PylRS of the invention) to be exported from the nucleus of a eukaryotic cell. Said export is believed to be mostly mediated by Crm1 (chromosomal region maintenance 1, also known as karyopherin exportin 1). NESs are known in the art. For example, the data-base ValidNESs (validness.ym.edu.tw/) provides sequence information of experimentally validated NES-containing proteins. Further, NES databases like, e.g., NESbase 1.0 (cbs.dtu.dk/databased/NESbase-1.0/; see Le Cour et al., Nucl Acids Res 31(1), 2003) as well as tools for NES prediction like NetNES (cbs.dtu.dk/services/NetNES/; see La Cour et al., La Cour et al., Protein Eng Des Sel 17(6):527-536, 2004), NESpredictor (NetNES, cbs.dtu.dk/; see Fu et al., Nucl Acids Res 41:D338-D343, 2013; La Cour et al., Protein Eng Des Sel 17(6):527-536, 2004)) and NESsential (a web interface combined with ValidNESs) are available to the public. Hydrophobic leucine-rich NESs are most common and represent the best characterized group of NESs to date. A hydrophobic leucine-rich NES is a non-conservative motif having 3 or 4 hydrophobic residues. Many of these NESs comprise the conserved amino acid sequence pattern LxxLxL (SEQ ID NO:4) or LxxxLxL (SEQ ID NO:5), wherein each L is independently selected from leucine, isoleucine, valine, phenylalanine and methionine amino acid residues, and each x is independently selected from any amino acid (see La Cour et al., Protein Eng Des Sel 17(6):527-536, 2004).

The term "nuclear localization signal" (abbreviated as "NLS", also referred to in the art as "nuclear localization sequence") refers to an amino acid sequence which can direct a polypeptide containing it (e.g., a wild-type archaeal PylRS) to be imported into the nucleus of a eukaryotic cell. Said export is believed to be mediated by binding of the NLS-containing polypeptide to importin (also known as karyopherin) so as to form a complex that moves through a nuclear pore. NLSs are known in the art. A multitude of NLS databases and tools for NLS prediction are available to the public, such as NLSdb (see Nair et al., Nucl Acids Res 31(1), 2003), cNLS Mapper (nls-mapper.aib.keio.ac.jp; see Kosugi et al., Proc Natl Acad Sci U S A. 106(25):10171-10176, 2009; Kosugi et al., J Biol Chem 284(1):478-485, 2009), SeqNLS (see Lin et al., PLoS One 8(10):e76864, 2013), and NucPred (sbc.su.se/~maccallr/nucpred/; see Branmeier et al., Bioinformatics 23(9):1159-60, 2007).

Archaeal PylRSs of the invention can be prepared by modifying the amino acid sequence of a naturally occurring archaeal PylRS, in particular by introducing one or more amino acid alteration (independently selected from amino acid substitutions, deletions and additions) which removes the NLS found in said naturally occurring PylRS and/or introduces at least one NES. The NLS in the naturally occurring PylRS can be identified using known NLS detection tools such as, e.g., cNLS Mapper.

The removal of a NLS from and/or the introduction of a NES into a polypeptide, such as an archaeal PylRS, can change the localization of the thus modified polypeptide when expressed in a eukaryotic cell, and in particular can avoid or reduce accumulation of the polypeptide in the nucleus of the eukaryotic cell. Thus, the localization of a PylRS of the invention expressed in a eukaryotic cell can be changed compared to a PylRS, which differs from the PylRS of the invention in that it (still) comprises the NLS and lacks the NES.

Where the archaeal PylRS of the invention comprises a NES but (still) comprises an NLS, the NES is preferably chosen such that the strength of the NES overrides the NLS preventing an accumulation of the PylRS in the nucleus of a eukaryotic cell.

Removal of the NLS from a wild-type or mutant PylRS and/or introduction of a NES into the wild-type or mutant PylRS so as to obtain a PylRS of the invention do not abrogate PylRS enzymatic activity. Preferably, PylRS enzymatic activity is maintained at basically the same level, i.e. the PylRS of the invention has at least 50%, at least 60%, at least 70%, at least 80%, at least 90%, or at least 95% of the enzymatic activity of the corresponding wild-type or mutant PylRS.

The NES is expediently located within the PylRS of the invention such that the NES is functional. For example, a NES can be attached to the C-terminus (e.g., C-terminal of the last amino acid residue) or the N-terminus (e.g., in between amino acid residue 1, the N-terminal methionine, and amino acid residue 2) of a wild-type or mutant archaeal PylRS.

NES sequences suitable in PylRS of the invention are known in the art (e.g., from NES databases). In one embodiment, the PylRS of the invention comprises a hydrophobic leucine-rich NES, in particular a NES comprising the amino acid sequence LxxLxL (SEQ ID NO:4) or LxxxLxL (SEQ ID NO:5), wherein each L is independently selected from leucine, isoleucine, valine, phenylalanine and methionine, and each x is independently selected from any amino acid; more particularly a NES comprising an amino acid sequence selected from $L^1xxL^2xxL^1xL^3$ (SEQ ID NO:6), $L^1xxxL^2xxL^1xL^3$ (SEQ ID NO:7), $L^1xxL^2xxxL^1xL^3$ (SEQ ID NO:8) and $L^1xxxL^2xxxL^1xL^3$ (SEQ ID NO:9), wherein $L^1$ is leucine, $L^2$ is selected from leucine, isoleucine, valine, phenylalanine and methionine, $L^3$ is selected from leucine and isoleucine, and each x is independently selected from any amino acid. Preferably, the NES comprises the amino acid sequence LPPLERLTL (SEQ ID NO:10) which is found in the HIV-1 Rev protein or, more preferably, the amino acid sequence ACPVPLQLPPLERLTLD (SEQ ID NO:11).

According to a particular embodiment, the PylRS of the invention comprises an enzymatically active fragment of the amino acid sequence of *M. mazei* PylRS$^{AF}$ set forth in SEQ ID NO:2, and a NES comprising the amino acid sequence of SEQ ID NO:10 or 11. A preferred example of such PylRS comprises or essentially consists of the amino acid sequence of SEQ ID NO:12.

```
                                                                   SEQ ID NO: 12
MACPVPLQLPPLERLTLDDKKPLNTLISATGLWMSRTGTIHKIKHHEVSRSKIYIEMACG    60

DHLVVNNSRSSRTARALRHHKYRKTCKRCRVSDEDLNKFLTKANEDQTSVKVKVVSAPTR   120

TKKAMPKSVARAPKPLENTEAAQAQPSGSKFSPAIPVSTQESVSVPASVSTSISSISTGA   180

TASALVKGNINPITSMSAPVQASAPALIKSQTDRLEVLLNPKDEISLNSGKPFRELESEL   240

LSRRKKDLQQIYAEERENYLGKLEREITRFFVDRGFLEIKSPILIPLEYIERMGIDNDTE   300

LSKQIFRVDKNFCLRPMLAPNLANYLRKLDRALPDPIKIFEIGPCYRKESDGKEHLEEFT   360

MLNFCQMGSGCTRENLESIITDFLNHLGIDFKIVGDSCMVFGDILDVMHGDLELSSAVVG   420

PIPLDREWGIDKPWIGAGFGLERLLKVKHDFKNIKRAARSESYYNGISTNL            471
(underlined: SEQ ID NO: 10, bold: SEQ ID NO: 11)
```

A further preferred example of such PylRS comprises or essentially consists of the amino acid sequence of SEQ ID NO:13.

```
                                                                   SEQ ID NO: 13
MDKKPLNTLISATGLWMSRIGTIHKIKHHEVSRSKIYIEMACGDHLVVNNSRSSRTARAL    60

RHHKYRKTCKRCRVSDEDLNKFLTKANEDQTSVKVKVVSAPTRTKKAMPKSVARAPKPLE   120

NTEAAQAQPSGSKFSPAIPVSTQESVSVPASVSTSISSISTGATASALVKGNINPITSMS   180

APVQASAPALIKSQTDRLEVLLNPKDEISLNSGKPFRELESELLSRRKKDLQQIYAEERE   240

NYLGKLEREITRFFVDRGFLEIKSPILIPLEYIERMGIDNDTELSKQIFRVDKNFCLRPM   300
```

```
                                                                -continued
LAPNLANYLRKLDRALPDPIKIFEIGPCYRKESDGKEHLEEFTMLNFCQMGSGCTRENLE     360

SIITDFLNHLGIDFKIVGDSCMVFGDILDVMHGDLELSSAVVGPIPLDREWGIDKPWIGA     420

GFGLERLLKVKHDFKNIKRAARSESYYNGISTNLACPVPLQLPPLERLTLD              471
(underlined: SEQ ID NO: 10, bold: SEQ ID NO: 11)
```

According to a particular embodiment, the PylRS of the invention comprises an enzymatically active fragment of the amino acid sequence of wildtype *M. mazei* PylRS set forth in SEQ ID NO:1, and a NES comprising the amino acid sequence of SEQ ID NO:10 or 11. A preferred example of such PylRS comprises or essentially consists of the amino acid sequence of SEQ ID NO:14.

```
                                                                SEQ ID NO: 14
MACPVPLQLPPLERLTLDDKKPLNTLISATGLWMSRTGTIHKIKHHEVSRSKIYIEMACG    60

DHLVVNNSRSSRTARALRHHKYRKTCKRCRVSDEDLNKFLTKANEDQTSVKVKVVSAPTR    120

TKKAMPKSVARAPKPLENTEAAQAQPSGSKFSPAIPVSTQESVSVPASVSTSISSISTGA    180

TASALVKGNTNPITSMSAPVQASAPALTKSQTDRLEVLLNPKDEISLNSGKPFRELESEL    240

LSRRKKDLQQIYAEERENYLGKLEREITRFFVDRGFLEIKSPILIPLEYIERMGIDNDTE    300

LSKQIFRVDKNFCLRPMLAPNLYNYLRKLDRALPDPIKIFEIGPCYRKESDGKEHLEEFT    360

MLNFCQMGSGCTRENLESIITDFLNHLGIDFKIVGDSCMVYGDILDVMHGDLELSSAVVG    420

PIPLDREWGIDKPWIGAGFGLERLLKVKHDFKNIKRAARSESYYNGISTNL             471
(underlined: SEQ ID NO: 10, bold: SEQ ID NO: 11)
```

A further preferred example of such PylRS comprises or essentially consists of the amino acid sequence of SEQ ID NO:15.

```
                                                                SEQ ID NO: 15
MDKKPLNTLISATGLWMSRIGTIHKIKHHEVSRSKIYIEMACGDHLVVNNSRSSRTARAL    60

RHHKYRKTCKRCRVSDEDLNKFLTKANEDQTSVKVKVVSAPTRTKKAMPKSVARAPKPLE    120

NTEAAQAQPSGSKFSPAIPVSTQESVSVPASVSTSISSISTGATASALVKGNINPITSMS    180

APVQASAPALIKSQTDRLEVLLNPKDEISLNSGKPFRELESELLSRRKKDLQQIYAEERE    240

NYLGKLEREITRFFVDRGFLEIKSPILIPLEYIERMGIDNDTELSKQIFRVDKNFCLRPM    300

LAPNLYNYLRKLDRALPDPIKIFEIGPCYRKESDGKEHLEEFTMLNFCQMGSGCTRENLE    360

SIITDFLNHLGIDFKIVGDSCMVYGDILDVMHGDLELSSAVVGPIPLDREWGIDKPWIGA    420

GFGLERLLKVKHDFKNIKRAARSESYYNGISTNLACPVPLQLPPLERLTLD             471
(underlined: SEQ ID NO:10, bold: SEQ ID NO: 11)
```

According to a further particular embodiment, the PylRS of the invention comprises an enzymatically active fragment of the amino acid sequence of *M. barkeri* PylRS set forth in SEQ ID NO:3, and a NES comprising the amino acid sequence of SEQ ID NO:10 or 11. A preferred example of such PylRS comprises or essentially consists of the amino acid sequence of SEQ ID NO:16.

```
                                                                SEQ ID NO: 16
MACPVPLQLPPLERLTLDDKKPLDVLISATGLWMSRTGILHKIKHHEVSRSKIYIEMACG    60

DHLVVNNSRSCRTARAFRHHKYRKICKRCRVSDEDINNFLIRSTESKNSVKVRVVSAPKV    120

KKAMPKSVSRAPKPLENSVSAKASTNTSRSVPSPAKSTPNSSVPASAPAPSLTRSQLDRV    180

EALLSPEDKISLNMAKPFRELEPELVIRRKNDFQRLYINDREDYLGKLERDITKFFVDRG    240
```

```
-continued

FLEIKSPILIPAEYVERMGINNDTELSKQIFRVDKNLCLRPMLAPTLYNYLRKLDRILPG    300

PIKIFEVGPCYRKESDGKEHLEEFTMVNFCQMGSGCTRENLEALIKEFLDYLEIDFEIVG    360

DSCMVYGDILDIMHGDLELSSAVVGPVSLDREWGIDKPWIGAGFGLERLLKVMHGFKNIK    420

RASRSESYYNGISTNL                                                436
(underlined: SEQ ID NO: 10, bold: SEQ ID NO: 11)
```

A further preferred example of such PylRS comprises or essentially consists of the amino acid sequence of SEQ ID NO:17.

```
                                                         SEQ ID NO: 17
MDKKPLDVLISATGLWMSRTGILHKIKHHEVSRSKIYIEMACGDHLVVNNSRSCRTARAF     60

RHHKYRKICKRCRVSDEDINNFLIRSTESKNSVKVRVVSAPKVKKAMPKSVSRAPKPLEN    120

SVSAKASINTSRSVPSPAKSTPNSSVPASAPAPSLIRSQLDRVEALLSPEDKISLNMAKP    180

FRELEPELVIRRKNDFQRLYINDREDYLGKLERDITKFFVDRGFLEIKSPILIPAEYVER    240

MGINNDTELSKQIFRVDKNLCLRPMLAPTLYNYLRKLDRILPGPIKIFEVGPCYRKESDG    300

KEHLEEFTMVNFCQMGSGCTRENLEALIKEFLDYLEIDFEIVGDSCMVYGDILDIMHGDL    360

ELSSAVVGPVSLDREWGIDKPWIGAGFGLERLLKVMHGFKNIKRASRSESYYNGISTNLA    420

CPVPLQLPPLERLTLD                                                436
(underlined: SEQ ID NO: 10, bold: SEQ ID NO: 11)
```

The PylRS of the invention are used in tRNA$^{Pyl}$/PylRS pairs, wherein the PylRS is capable of acylating the tRNA$^{Pyl}$, preferably with an UAA or a salt thereof.

Unless indicated otherwise, "tRNA$^{Pyl}$", as used herein, refers to a tRNA that can be acylated (preferably selectively) by a PylRS of the invention. The tRNA$^{Pyl}$ described herein in the context of the present invention may be a wildtype tRNA that can be acylated by a PylRS with pyrrolysine, or a mutant of such tRNA, e.g., a wildtype or a mutant tRNA from an archaeon, for example from a *Methanosarcina* species, e.g. *M. mazei* or *M. barkeri*. For site-specific incorporation of the UAA into POI, the anticodon comprised by the tRNA$^{Pyl}$ used together with the PylRS of the invention is expediently the reverse complement of a selector codon. In particular embodiments, the anticodon of the tRNA$^{Pyl}$ is the reverse complement of the amber stop codon. For other applications such as, e.g., proteome labeling (Elliott et al., Nat Biotechnol 32(5):465-472, 2014), the anticodon comprised by the tRNA$^{Pyl}$ used together with the PylRS of the invention may be a codon recognized by endogenous tRNAs of the eukaryotic cells.

The term "selector codon" as used herein refers to a codon that is recognized (i.e. bound) by the tRNA$^{Pyl}$ in the translation process and is not recognized by endogenous tRNAs of the eukaryotic cell. The term is also used for the corresponding codons in polypeptide-encoding sequences of polynucleotides which are not messenger RNAs (mRNAs), e.g. DNA plasmids. Preferably, the selector codon is a codon of low abundance in naturally occurring eukaryotic cells. The anticodon of the tRNA$^{Pyl}$ binds to a selector codon within an mRNA and thus incorporates the UAA site-specifically into the growing chain of the polypeptide encoded by said mRNA. The known 64 genetic (triplet) codons code for 20 amino acids and three stop codons. Because only one stop codon is needed for translational termination, the other two can in principle be used to encode non-proteinogenic amino acids. For example, the amber codon, UAG, has been successfully used as a selector codon in in vitro and in vivo translation systems to direct the incorporation of unnatural amino acids. Selector codons utilized in methods of the present invention expand the genetic codon framework of the protein biosynthetic machinery of the translation system used. Specifically, selector codons include, but are not limited to, nonsense codons, such as stop codons, e.g., amber (UAG), ochre (UAA), and opal (UGA) codons; codons consisting of more than three bases (e.g., four base codons); and codons derived from natural or unnatural base pairs. For a given system, a selector codon can also include one of the natural three base codons (i.e. natural triplets), wherein the endogenous translation system does not (or only scarcely) use said natural triplet, e.g., a system that is lacking a tRNA that recognizes the natural triplet or a system wherein the natural triplet is a rare codon.

A recombinant tRNA that alters the reading of an mRNA in a given translation system (e.g. a eukaryotic cell) such that it allows for reading through, e.g., a stop codon, a four base codon, or a rare codon, is termed suppressor tRNA. The suppression efficiency for a stop codon serving as a selector codon (e.g., the amber codon) depends upon the competition between the (aminoacylated) tRNA$^{Pyl}$ (which acts as suppressor tRNA) and the release factor (e.g. RF1) which binds to the stop codon and initiates release of the growing polypeptide chain from the ribosome. Suppression efficiency of such stop codon can therefore be increased using a release factor-(e.g. RF1-)deficient strain.

A polynucleotide sequence encoding a target polypeptide (also referred to herein as polypeptide of interest or POI) can comprise one or more, e.g., two or more, more than three, etc., codons (e.g. selector codons) which are the reverse complement of the anticodon comprised by the tRNA$^{Pyl}$. Conventional site-directed mutagenesis can be used to introduce said codon(s) at the site of interest into a polynucleotide sequence so as to generate a POI-encoding polynucleotide sequence.

A POI comprising one or more than one UAA residue can be prepared according to the present invention using a eukaryotic cell. The eukaryotic cell comprises (e.g., is fed with) at least one unnatural amino acid or a salt thereof corresponding to the UAA residue(s) of the POI to be prepared. The eukaryotic cell further comprises:
  (i) a PylRS of the invention and a tRNA$^{Pyl}$, wherein the PylRS is capable of (preferably selectively) acylating the tRNA$^{Pyl}$ with the UAA or salt thereof; and
  (ii) a polynucleotide encoding the POI, wherein any position of the POI occupied by an UAA residue is encoded by a codon (e.g. selector codon) that is the reverse complement of the anticodon of the tRNA$^{Pyl}$.

The eukaryotic cell is cultured so as to allow translation of the POI-encoding polynucleotide (ii), thereby producing the POI.

For producing a POI (target polypeptide) according to a method of the present invention, the translation in step (b) can be achieved by culturing the eukaryotic cell under suitable conditions, preferably in the presence of (e.g., in a culture medium containing) the UAA or salt thereof, for a time suitable to allow translation at a ribosome of the cell. Depending on the polynucleotide(s) encoding the POI (and optionally the PylRS, tRNA$^{Pyl}$), it may be required to induce expression by adding a compound inducing transcription, such as, e.g., arabinose, isopropyl β-D-thiogalactoside (IPTG) or tetracycline. mRNA that encodes the target polypeptide (and comprises one or more than codon that is the reverse complement of the anticodon comprised by the tRNA$^{Pyl}$) is bound by the ribosome. Then, the polypeptide is formed by stepwise attachment of amino acids and UAAs at positions encoded by codons which are recognized (bound) by respective aminoacyl tRNAs. Thus, the UAA(s) is/are incorporated in the target polypeptide at the position(s) encoded by the codon(s) that is/are the reverse complement of the anticodon comprised by the tRNA$^{Pyl}$.

The eukaryotic cell may comprise a polynucleotide sequence encoding the PylRS of the invention which allows for expression of the PylRS by the cell. Likewise, the tRNA$^{Pyl}$ may be produced by the eukaryotic cell based on a tRNA$^{Pyl}$-encoding polynucleotide sequence comprised by the cell. The PylRS-encoding polynucleotide sequence and the tRNA$^{Pyl}$-encoding polynucleotide sequence can be located either on the same polynucleotide or on separate polynucleotides.

Thus, in one embodiment, the present invention provides a method for producing a POI comprising one or more than one UAA residue, wherein the method comprises the steps of:
  (a) providing a eukaryotic cell comprising polynucleotide sequences encoding:
    at least one PylRS of the invention,
    at least one tRNA (tRNA$^{Pyl}$) that can be acylated by the PylRS, and
    at least one POI, wherein any position of the POI occupied by an UAA residue is encoded by a codon that is the reverse complement of the anticodon of the tRNA$^{Pyl}$; and
  (b) allowing for translation of the polynucleotide sequences by the eukaryotic cell in the presence of an UAA or a salt thereof, thereby producing the PylRS, tRNA$^{Pyl}$ and the POI.

The eukaryotic cells used for preparing a POI comprising one or more than one unnatural amino acid residue as described herein can be prepared by introducing polynucleotide sequences encoding the PylRS, the tRNA$^{Pyl}$ and the POI into a eukaryotic (host) cell. Said polynucleotide sequences can be located on the same polynucleotide or on separate polynucleotides, and can be introduced into the cell by methods known in the art (such as, e.g., using virus-mediated gene delivery, electroporation, microinjection, lipofection, or others).

The present invention also provides polynucleotides encoding the PylRS of the invention. In addition to the PylRS of the invention, such polynucleotide may encode a tRNA$^{Pyl}$ that can be acylated by the PylRS.

The present invention further provides combinations of at least one polynucleotide encoding a PylRS of the invention and at least one polynucleotide encoding a tRNA$^{Pyl}$ that can be acylated by said PylRS.

The polynucleotides of the invention as well as the tRNA$^{Pyl}$-and/or POI-encoding polynucleotides used in the context of the present invention are preferably expression vectors suitable for transfecting a eukaryotic cell and allowing for the expression of the encoded PylRS, tRNA$^{Pyl}$ and POI, respectively, in said cell.

The present invention also provides a eukaryotic cell capable of expressing a PylRS of the invention. In particular, the present invention provides a eukaryotic cell comprising a polynucleotide or combination of polynucleotides, wherein said polynucleotide(s) encode(s) the PylRS of the invention and a tRNA$^{Pyl}$, wherein the tRNA$^{Pyl}$ is a tRNA that can be acylated (preferably selectively) by the PylRS. Expediently, the eukaryotic cell of the invention is capable of expressing both the tRNA$^{Pyl}$ and the PylRS of the invention, wherein the PylRS is capable of acylating the tRNA$^{Pyl}$ (preferably selectively) with an amino acid, e.g. with an UAA.

Eukaryotic cells of the present invention can be selected from, but are not limited to, mammalian cells, insect cells, yeast cells and plant cells. The eukaryotic cells of the invention may be present as individual cells or may be part of a tissue (e.g. a cell in a (cultured) tissue, organ or entire organism).

The PylRS and tRNA$^{Pyl}$ of the present invention are preferably orthogonal.

The term "orthogonal" as used herein refers to a molecule (e.g., an orthogonal tRNA and/or an orthogonal RS) that is used with reduced efficiency by a translation system of interest (e.g., a eukaryotic cell used for expression of a POI as described herein). "Orthogonal" refers to the inability or reduced efficiency, e.g., less than 20% efficient, less than 10% efficient, less than 5% efficient, or e.g., less than 1% efficient, of an orthogonal tRNA or an orthogonal RS to function with the endogenous RSs or endogenous tRNAs, respectively, of the translation system of interest.

Accordingly, in particular embodiments of the invention, any endogenous RS of the eukaryotic cell of the invention catalyzes acylation of the (orthogonal) tRNA$^{Pyl}$ with reduced or even zero efficiency, when compared to acylation of an endogenous tRNA by the endogenous RS, for example less than 20% as efficient, less than 10% as efficient, less than 5% as efficient or less than 1% as efficient. Alternatively or additionally, the (orthogonal) PylRS of the invention acylates any endogenous tRNA of the eukaryotic cell of the invention with reduced or even zero efficiency, as compared to acylation of the tRNA$^{Pyl}$ by an endogenous RS of the cell, for example less than 20% as efficient, less than 10% as efficient, less than 5% as efficient or less than 1% as efficient.

Unless indicated differently, the terms "endogenous tRNA" and "endogenous aminoacyl tRNA synthetase" ("endogenous RS") used therein refer to a tRNA and an RS, respectively, that was present in the cell ultimately used as translation system prior to introducing the PylRS of the invention and the tRNA$^{Pyl}$, respectively, used in the context of the present invention.

The term "translation system" generally refers to a set of components necessary to incorporate a naturally occurring amino acid in a growing polypeptide chain (protein). Components of a translation system can include, e.g., ribosomes, tRNAs, aminoacyl tRNA synthetases (RS), mRNA and the like. Translation systems include artificial mixture of said components, cell extracts and living cells, e.g. living eukaryotic cells.

The pair of PylRS and tRNA$^{Pyl}$ used for preparing a POI according to the present invention is preferably orthogonal in that the tRNA$^{Pyl}$, in the eukaryotic cell used for preparing the POI, is preferentially acylated by the PylRS of the invention with an UAA or a salt thereof (UAA). Expediently, the orthogonal pair functions in said eukaryotic cell such that the cell uses the UAA-acylated tRNA$^{Pyl}$ to incorporate the UAA residue into the growing polypeptide chain of the POI. Incorporation occurs in a site-specific manner, e.g., the tRNA$^{Pyl}$ recognizes a codon (e.g., a selector codon such as an amber stop codon) in the mRNA coding for the POI.

As used herein, the term "preferentially acylated" refers to an efficiency of, e.g., about 50% efficient, about 70% efficient, about 75% efficient, about 85% efficient, about 90% efficient, about 95% efficient, or about 99% or more efficient, at which the PylRS acylates the tRNA$^{Pyl}$ with an UAA compared to an endogenous tRNA or amino acid of a eukaryotic cell. The UAA is then incorporated into a growing polypeptide chain with high fidelity, e.g., at greater than about 75%, greater than about 80%, greater than about 90%, greater than about 95%, or greater than about 99% or more efficiency for a given codon (e.g., selector codon) that is the reverse complement of the anticodon comprised by the tRNA$^{Pyl}$.

tRNA$^{Pyl}$/PylRS pairs suitable in producing a POI according to the present invention may be selected from libraries of mutant tRNA and PylRSs, e.g. based on the results of a library screening. Such selection may be performed analogous to known methods for evolving tRNA/RS pairs described in, e.g., WO 02/085923 and WO 02/06075. To generate a tRNA$^{Pyl}$/PylRS pair of the invention, one may start from a wild-type or mutant archaeal PylRS that (still) comprises a nuclear localization signal and lacks a NES, and remove the nuclear localization signal and/or introduce a NES prior to or after a suitable tRNA$^{Pyl}$/PylRS pair is identified.

After translation, the target polypeptide prepared according to the present invention may optionally be recovered and purified, either partially or substantially to homogeneity, according to procedures generally known in the art. Unless the target polypeptide is secreted into the culture medium, recovery usually requires cell disruption. Methods of cell disruption are well known in the art and include physical disruption, e.g., by (ultrasound) sonication, liquid-sheer disruption (e.g., via French press), mechanical methods (such as those utilizing blenders or grinders) or freeze-thaw cycling, as well as chemical lysis using agents which disrupt lipid-lipid, protein-protein and/or protein-lipid interactions (such as detergents), and combinations of physical disruption techniques and chemical lysis. Standard procedures for purifying polypeptides from cell lysates or culture media are also well known in the art and include, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. Antibodies made against the polypeptides of the invention can be used as purification reagents, i.e. for affinity-based purification of the polypeptides. A variety of purification/protein folding methods are well known in the art, including, e.g., those set forth in Scopes, Protein Purification, Springer, Berlin (1993); and Deutscher, Methods in Enzymology Vol. 182: Guide to Protein Purification, Academic Press (1990); and the references cited therein.

As noted, those of skill in the art will recognize that, after synthesis, expression and/or purification, polypeptides can possess a conformation different from the desired conformations of the relevant polypeptides. For example, polypeptides produced by prokaryotic systems often are optimized by exposure to chaotropic agents to achieve proper folding. During purification from, e.g., lysates derived from E. coli, the expressed polypeptide is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art. Polypeptides can be refolded in a redox buffer containing, e.g., oxidized glutathione and L-arginine.

The term "unnatural amino acid" (abbreviated "UAA"), as used herein, refers to an amino acid that is not one of the 20 canonical amino acids or selenocysteine or pyrrolysine. The term also refers to amino acid analogs, e.g. compounds which differ from amino acids such that the a-amino group is replaced by a hydroxyl group and/or the carboxylic acid function forms an ester. When translationally incorporated into a polypeptide, said amino acid analogs yield amino acid residues which are different from the amino acid residues corresponding to the 20 canonical amino acids or selenocysteine or pyrrolysine. When UAAs which are amino acid analogs wherein the carboxylic acid function forms an ester of formula —C(O)—O—R are used for preparing polypeptides in a translation system (such as a eukaryotic cell), it is believed that R is removed in situ, for example enzymatically, in the translation system prior of being incorporated in the POI. Accordingly, R is expediently chosen so as to be compatible with the translation system's ability to convert the UAA or salt thereof into a form that is recognized and processed by the PylRS of the invention.

UAAs useful in methods and kits of the present invention have been described in the prior art (for review see e.g. Liu et al., Annu Rev Biochem 83:379-408, 2010, Lemke, ChemBioChem 15:1691-1694, 2014).

The UAAs may comprise a group (herein referred to as "labeling group") that facilitates reaction with a suitable group (herein referred to as "docking group") of another molecule (herein termed "conjugation partner molecule") so as to covalently attach the conjugation partner molecule to the UAA. When a UAA comprising a labeling group is translationally incorporated into a target polypeptide, the labeling group becomes part of the target polypeptide. Accordingly, a target polypeptide prepared according to the method of the present invention can be reacted with one or more than one conjugation partner molecule such that the conjugation partner molecules bind covalently to the (labeling groups of the) unnatural amino acid residue(s) of the target polypeptide. Such conjugation reactions may be used for in situ coupling of target polypeptides within a cell or tissue expressing the target polypeptide, or for site-specific conjugation of isolated or partially isolated target polypeptides.

Particular useful choices for combinations of labeling groups and docking groups (of conjugation partner molecules) are those which can react by metal-free click reactions. Such click reactions include strain-promoted inverse-electron-demand Diels-Alder cycloadditions (SPIEDAC; see, e.g., Devaraj et al., Angew Chem Int Ed Engl 2009, 48:7013)) as well as cycloadditions between strained cycloalkynyl groups, or strained cycloalkynyl analog groups having one or more of the ring atoms not bound by the triple bond substituted by amino groups), with azides, nitrile oxides, nitrones and diazocarbonyl reagents (see, e.g., Sanders et al., J Am Chem Soc 2010, 133:949; Agard et al., J Am Chem Soc 2004, 126:15046), for example strain promoted alkyne-azide cycloadditions (SPAAC). Such click reactions allow for ultrafast and biorthogonal covalent site-specific coupling of UAA labeling groups of target polypeptides with suitable groups of coupling partner molecule.

Pairs of docking and labeling groups which can react via the above-mentioned click reactions are known in the art. Examples of suitable UAAs comprising docking groups include, but are not limited to, the UAAs described, e.g., in WO 2012/104422 and WO 2015/107064.

Examples of particular suitable pairs of docking groups (comprised by the conjugation partner molecule) and labeling groups (comprised by the UAA residue(s) of the POI) include but are not limited to:

(a) a docking group comprising (or essentially consisting of) a group selected from an azido group, a nitrile oxide functional group (i.e. a radical of formula, a nitrone functional group or a diazocarbonyl group, combined with a labeling group comprising (or essentially consisting of) an optionally substituted strained alkynyl group (such groups can react covalently in a copper-free strain promoted alkyne-azide cycloaddition (SPAAC));

(b) a docking group comprising (or essentially consisting of) an optionally substituted strained alkynyl group, combined with a labeling group comprising (or essentially consisting of) a group selected from an azido group, a nitrile oxide functional group (i.e. a radical of formula, a nitrone functional group or a diazocarbonyl group (such groups can react covalently in a copper-free strain promoted alkyne-azide cycloaddition (SPAAC));

(c) a docking group comprising (or essentially consisting of) a group selected from optionally substituted strained alkynyl groups, optionally substituted strained alkenyl groups and norbornenyl groups, combined with a labeling group comprising (or essentially consisting of) an optionally substituted tetrazinyl group (such groups can react covalently in a copper-free strain promoted inverse-electron-demand Diels-Alder cycloaddition (SPIEDAC)).

(d) a docking group comprising (or essentially consisting of) an optionally substituted tetrazinyl group, combined with a labeling group comprising (or essentially consisting of) a group selected from optionally substituted strained alkynyl groups, optionally substituted strained alkenyl groups and norbornenyl groups (such groups can react covalently in a copper-free strain promoted inverse-electron-demand Diels-Alder cycloaddition (SPIEDAC)).

Optionally substituted strained alkynyl groups include, but are not limited to, optionally substituted trans-cyclooctenyl groups, such as those described in. Optionally substituted strained alkenyl groups include, but are not limited to, optionally substituted cyclooctynyl groups, such as those described in WO 2012/104422 and WO 2015/107064. Optionally substituted tetrazinyl groups include, but are not limited to, those described in WO 2012/104422 and WO 2015/107064.

An azido group is a radical of formula $-N_3$.

A nitrone functional group is a radical of formula $-C(R^x)=N^+(R^y)-O^-$, wherein $R^x$ hd and $R^y$ are organic residues, e.g., residues independently selected from $C_1-C_6$-alkyl as described herein.

A diazocarbonyl group is a radical of formula $-C(O)-CH=N_2$.

A nitrile oxide functional group is a radical of formula $-C\equiv N^+-O^-$ or, preferably, of formula $-C=N^+(R^x)-O^-$, wherein $R^x$ is an organic residue, e.g., a residue selected from $C_1-C_6$-alkyl as described herein.

"Cyclooctynyl is an unsaturated cycloaliphatic radical having 8 carbon atoms and one triple bond in the ring structure.

"Trans-cyclooctenyl" is an unsaturated cycloaliphatic radical having 8 carbon atoms and one double bond that is in trans configuration in the ring structure.

"Tetrazinyl" is a 6-membered monocyclic aromatic radical having 4 nitrogen ring atoms and 2 carbon ring atoms.

Unless indicated otherwise, the term "substituted" means that a radical is substituted with 1, 2 or 3, especially 1 or 2, substituent(s). In particular embodiments, these substituents can be selected independently from hydrogen, halogen, $C_1-C_4$-alkyl, $(R^aO)_2P(O)O-C_1-C_4$-alkyl, $(R^bO)_2P(O)-C_1-C_4$-alkyl, $CF_3$, CN, hydroxyl, $C_1-C_4$-alkoxy, $-O-CF_3$, $C_2-C_5$-alkenoxy, $C_2-C_5$-alkanoyloxy, $C_1-C_4$-alkylaminocarbonyloxy or $C_1-C_4$-alkylthio, $C_1-C_4$-alkylamino, di-($C_1-C_4$-alkyl)amino, $C_2-C_5$-alkenylamino, $N-C_2-C_5$-alkenyl-N-$C_1-C_4$-alkyl-amino and di-($C_2-C_5$-alkenyl)amino, wherein $R^a$ and $R^b$ $R^a$, $R^b$ are independently hydrogen or $C_2-C_5$-alkanoyloxymethyl.

The term halogen denotes in each case a fluorine, bromine, chlorine or iodine radical, in particular a fluorine radical.

$C_1-C_4$-Alkyl is a straight-chain or branched alkyl group having from 1 to 4, in particular from 1 to 3 carbon atoms. Examples include methyl and $C_2-C_4$-alkyl such as ethyl, n-propyl, iso-propyl, n-butyl, 2-butyl, iso-butyl and tert-butyl.

$C_2-C_5$-Alkenyl is a singly unsaturated hydrocarbon radical having 2, 3, 4 or 5 carbon atoms. Examples include vinyl, allyl (2-propen-1-yl), 1-propen-1-yl, 2-propen-2-yl, methallyl (2-methylprop-2-en-1-yl), 1-methylprop-2-en-1-yl, 2-buten-1-yl, 3-buten-1-yl, 2-penten-1-yl, 3-penten-1-yl, 4-penten-1-yl, 1-methylbut-2-en-1-yl and 2-ethylprop-2-en-1-yl.

$C_1-C_4$-Alkoxy is a radical of formula R—O—, wherein R is a $C_1-C_4$-alkyl group as defined herein.

$C_2-C_5$-Alkenoxy is a radical of formula R—O—, wherein R is $C_2-C_5$-alkenyl as defined herein.

$C_2-C_5$-Alkanoyloxy is a radical of formula R—C(O)—O—, wherein R is $C_1-C_4$-alkyl as defined herein.

$C_1-C_4$-Alkylaminocarbonyloxy is a radical of formula R—NH—C(O)—O—, wherein R is $C_1-C_4$-alkyl as defined herein.

$C_1$—$C_4$-Alkylthio is a radical of formula R—S—, wherein R is $C_1$—$C_4$-alkyl as defined herein.

$C_1$—$C_4$-Alkylamino is a radical of formula R—NH—, wherein R is $C_1$—$C_4$-alkyl as defined herein.

Di-($C_1$—$C_4$-alkyl)amino is a radical of formula $R^x$—N($R^y$)—, wherein $R^x$ and $R^y$ are independently $C_1$—$C_4$-alkyl as defined herein.

$C_2$—$C_5$-Alkenylamino is a radical of formula R—NH—, wherein R is $C_2$—$C_5$-alkenyl as defined herein.

N—$C_2$—$C_5$-alkenyl-N—$C_1$—$C_4$-alkyl-amino is a radical of formula $R^x$—N($R^y$)—, wherein $R^x$ is $C_2$—$C_5$-alkenyl as defined herein and $R^y$ is $C_1$—$C_4$-alkyl as defined herein.

Di-($C_2$—$C_5$-alkenyl)amino is a radical of formula $R^x$—N($R^y$)—, wherein $R^x$ and $R^y$ are independently $C_2$—$C_5$-alkenyl as defined herein.

$C_2$—$C_5$-Alkanoyloxymethyl is a radical of formula $R^x$—C(O)—O—$CH_2$—, wherein $R^x$ is $C_1$—$C_4$-alkyl as defined herein.

The UAAs used in the context of the present invention can be used in the form of their salt. Salts of an UAA as described herein mean acid or base addition salts, especially addition salts with physiologically tolerated acids or bases. Physiologically tolerated acid addition salts can be formed by treatment of the base form of an UAA with appropriate organic or inorganic acids. UAAs containing an acidic proton may be converted into their non-toxic metal or amine addition salt forms by treatment with appropriate organic and inorganic bases. The UAAs and salts thereof described in the context of the present invention also comprise the hydrates and solvent addition forms thereof, e.g. hydrates, alcoholates and the like.

Physiologically tolerated acids or bases are in particular those which are tolerated by the translation system used for preparation of POI with UAA residues, e.g. are substantially non-toxic to living eukaryotic cells.

UAAs, and salts thereof, useful in the context of the present the invention can be prepared by analogy to methods which are well known in the art and are described, e.g., in the various publications cited herein.

The nature of the coupling partner molecule depends on the intended use. For example, the target polypeptide may be coupled to a molecule suitable for imaging methods or may be functionalized by coupling to a bioactive molecule. For instance, in addition to the docking group, a coupling partner molecule may comprise a group that selected from, but are not limited to, dyes (e.g. fluorescent, luminescent, or phosphorescent dyes, such as dansyl, coumarin, fluorescein, acridine, rhodamine, silicon-rhodamine, BODIPY, or cyanine dyes), molecules able to emit fluorescence upon contact with a reagent, chromophores (e.g., phytochrome, phycobilin, bilirubin, etc.), radiolabels (e.g. radioactive forms of hydrogen, fluorine, carbon, phosphorous, sulphur, or iodine, such as tritium, $^{18}$F, $^{11}$C, $^{14}$C, $^{32}$P, $^{33}$P, $^{33}$S, $^{35}$S, $^{11}$In, $^{125}$I, $^{123}$I, $^{131}$I, $^{212}$B, $^{90}$Y or $^{186}$Rh), MRI-sensitve spin labels, affinity tags (e.g. biotin, His-tag, Flag-tag, strep-tag, sugars, lipids, sterols, PEG-linkers, benzylguanines, benzylcytosines, or co-factors), polyethylene glycol groups (e.g., a branched PEG, a linear PEG, PEGs of different molecular weights, etc.), photocrosslinkers (such as p-azidoiodoacetanilide), NMR probes, X-ray probes, pH probes, IR probes, resins, solid supports and bioactive compounds (e.g. synthetic drugs). Suitable bioactive compounds include, but are not limited to, cytotoxic compounds (e.g., cancer chemotherapeutic compounds), antiviral compounds, biological response modifiers (e.g., hormones, chemokines, cytokines, interleukins, etc.), microtubule affecting agents, hormone modulators, and steroidal compounds. Specific examples of useful coupling partner molecules include, but are not limited to, a member of a receptor/ligand pair; a member of an antibody/antigen pair; a member of a lectin/carbohydrate pair; a member of an enzyme/substrate pair; biotin/avidin; biotin/streptavidin and digoxin/antidigoxin.

The ability of certain (labeling groups of) UAA residues to be coupled covalently in situ to (the docking groups of) conjugation partner molecules, in particular by a click reaction as described herein, can be used for detecting a target polypeptide having such UAA residue(s) within a eukaryotic cell or tissue expressing the target polypeptide, and for studying the distribution and fate of the target polypeptides. Specifically, the method of the present invention for preparing a target polypeptide by expression in eukaryotic cells can be combined with super-resolution microscopy (SRM) to detect the target polypeptide within the cell or a tissue of such cells. Several SRM methods are known in the art and can be adapted so as to utilize click chemistry for detecting a target polypeptide expressed by a eukaryotic cell of the present invention. Specific examples of such SRM methods include DNA-PAINT (DNA point accumulation for imaging in nanoscale topography; described, e.g., by Jungmann et al., Nat Methods 11:313-318, 2014), dSTORM (direct stochastic optical reconstruction microscopy) and STED (stimulated emission depletion) microscopy.

The present invention also provides kits comprising a polynucleotide encoding a PylRS of the present invention or a eukaryotic cell capable of expressing such PylRS. The kit of the invention may further comprise at least one unnatural amino acid, or a salt thereof, which can be used for acylating a tRNA in a reaction catalyzed by the PylRS. The kit of the invention may also comprise a tRNA that can be acylated by the PylRS (tRNA$^{Pyl}$). Kits of the invention can be used in methods for preparing UAA-residue containing target polypeptides or conjugates thereof as described herein.

EXAMPLES

Methods
(A) Synthesis of UAA
Compound 2 (TCO*) was prepared as described in WO 2015/107064.
(B) Cell culture, transfections and feeding with UAAs
HEK293T cells (ATCC CRL-3216) and COS-7 cells (ATCC, CRL-1651) were maintained in Dulbecco's modified Eagle's medium (Life Technologies, 41965-039) supplemented with 1% penicillin-streptomycin (Sigma, 10,000 U/ml penicillin, 10 mg/ml streptomycin, 0.9% NaCl), 2 mM L-glutamine (Sigma), 1 mM sodium pyruvate (Life Technologies) and 10% FBS (Sigma). Cells were cultured at 37° C. in a 5% $CO_2$ atmosphere and passaged every 2-3 days up to 15-20 passages.

In all cases, cells were seeded 15-20 h prior to transfection at a density resulting in 70-80% confluency at the time of transfection. Chambers for HEK293T experiments were coated with poly-L-lysine (Sigma) as described in Nikic et al. (Nat Protoc 10(5):780-791, 2015)). Immunolabeling and FISH were performed on 24-well plates with glass bottom (Greiner Bio-One).

All transfections were done using the JetPrime reagent (PeqLab) according to the manufacturer's recommendations.

Stock and working solutions for all of the used UAAs were prepared as described in Nikic et al. (Nat Protoc 10(5):780-791, 2015). Unless otherwise stated, final UAA concentration in the cell culture medium was 250 µM.

(C) Preparation of Anti-PylRS Antibody

E. coli BL21(DE3)A1 cells were transformed with the plasmid pTXB3-6His-TEV-PylRS$^{AF}$ and the encoded His-tagged fusion of M. mazei PylRS$^{AF}$ and TEV (His$_6$-TEV-PylRS$^{AF}$) was recombinantly expressed in TB medium overnight at 18° C. after induction with 0.02% arabinose and 1 mM IPTG. Cells were harvested by centrifugation, resuspended in 4× PBS (pH 8, 1 mM PMSF, 0.2 mM TCEP) and lysed using a high pressure homogenizer. Debris was removed by centrifugation and His$_6$-TEV-PylRS$^{AF}$ was purified from the clear supernatant by incubation with Ni-NTA magnetic beads for 1 h at 4° C., washing with increasing imidazole concentrations, and elution with 400 mM imidazole in 4× PBS. The protein containing elution fraction was concentrated using a protein filter device (Spin-X UF, Corning, 30 kDa cutoff). The protein was further purified using preparative gel filtration chromatography (Superdex 200, GE Healthcare). The protein containing fractions were concentrated and used for immunization of two rats (Eurogentec). The resulting polyclonal anti-PylRS antibody was used for detecting PylRS$^{AF}$ and variants therefore in the examples described herein.

(D) Flow Cytometry

Unless stated otherwise, cells were harvested two days after transfection, resuspended in 1× PBS and passed through 70 µm cell strainers. Co-transfections for flow cytometry were performed with a plasmid encoding the POI (including a TAG codon encoding the amino acid position to be occupied by the UAA), a plasmid encoding the tRNA$^{Pyl}$ having the anticodon CUA (hereinafter simply referred to as tRNA$^{Pyl}$) and a plasmid encoding the PylRS or variant thereof, respectively, at a 1:1:1 ratio with 1.2 µg total DNA. Cell culture medium was exchanged for fresh medium containing the UAA 4-6 h post-transfection and left until the time of harvesting. Data acquisition and analysis were performed using a LSRFortessa SORP Cell Analyzer (Becton, Dickinson and Company) and the FlowJo software (FlowJo). Cells were gated first by cell type (using FSC-A× SSC-A parameters) and then by single cell (FSC-A×SSC-W). GFP fluorescence was acquired in the 488-530/30 channel and iRFP fluorescence in the 640-730/45 channel.

(E) PylRS immunostaining and imaging, fluorescence in situ hybridization (FISH)

One day after transfection, the cells were fixed in 2% paraformaldehyde in 1× PBS for 10 min at RT, and then permeabilized in 0.5% Triton in 1× PBS for 15 min at RT. The permeabilized cell samples were incubated for 90 min in blocking solution (3% BSA in 1× PBS for 90 min at RT), and then with the primary antibody (polyclonal anti-PylRS, prepared as described herein, 1 µg/ml in blocking solution) overnight at 4° C. The next day, the cell samples were washed with 1× PBS and incubated with secondary antibody (Thermo Fisher Scientific, goat anti-rat IgG(H+L) Alexa Fluor 594 conjugate, 2 µg/ml in blocking solution) for 60 min at RT. DNA was stained with Hoechst 33342 (1 µg/ml in 1× PBS) for 10 min at RT.

Fluorescence in situ hybridization (FISH) experiments were performed one day after transfection. The hybridization protocol was adapted for 24-well plates from Pierce et al., Methods Cell Biol 122:415-436, 2014). The hybridization probe (5'-CTAACCCGGCTGAACGGATT-TAGAGTCCATTCGATC-3', labelled at the 5' terminus with digoxigenin; SEQ ID NO:18) was used at 0.16 µM. After the washes with SSC, cells were incubated for 1 h at RT in blocking buffer (0.1 M TrisHCl, 150 mM NaCl, 1× blocking reagent (Sigma 000000011096176001). Then, cells were incubated with an anti-digoxigenin-fluorescein antibody conjugate (Sigma 000000011207741910) at a 1:200 dilution in blocking buffer overnight at 4° C. The next day, 3 washes of 5 minutes were done in Tween buffer (0.1 M TrisHCl, 150 mM NaCl, 0.5% Tween20). Finally, DNA was stained with Hoechst 33342 (1 µg/ml in 1× PBS) for 10 min at RT.

Confocal images were acquired on a Leica SP8 STED 3× microscope using the 405 nm (for Hoechst 33342) and 594 nm (for Alexa594) laser lines for excitation. Emission light was collected with HyD detectors at 420-500 nm and 605-680 nm respectively.

(F) Vimentin and Nup153: constructs and transfections

Specific mutations were introduced into the plasmid DNA sequence of constructs of interest by PCR-based site-directed mutagenesis, thus generating in-frame amber codons in the cDNA. For vimentin, the pVimentin-PSmOrange plasmid (Addgene plasmid #31922; Subach et al., Nat Methods 8:771-777, 2011) was mutated at position N116 of vimentin, thus generating the pVimentin$^{N116TAG}$-PSmOrange construct. For Nup153, a pGFP-Nup153 plasmid was constructed by inserting a codon-optimized Nup153 cDNA into a pEGFP backbone. Subsequently, position N149 of the GFP gene was mutated, thus generating the pGFP$^{N149TAG}$-Nup153 construct. For the expression of the amber suppression system in mammalian cells, the cells were transfected with the pcDNA3.1 tRNA$^{Pyl}$/NES-PylRS$^{AF}$ plasmid.

For Click-PAINT experiments, cells were co-transfected with pcDNA3.1 tRNA$^{Pyl}$/NES-PylRS$^{AF}$ and either pVimentin$^{N116TAG}$-PSmOrange or pGFP$^{N149TAG}$-Nup153 and at ratio of a 1:1 using method (B) described herein. UAA 2 (TCO*) was added immediately after transfections. 8-10 hours after transfection, the cell culture medium was exchanged and cells were cultured overnight with fresh UAA solution. Approximately 30-36 h after transfection, the cell culture medium was exchanged for fresh medium and cells were cultured overnight without UAA.

(G) Click-PAINT Labeling

Approximately 48 h after transfection, the cells were rinsed with PBS, fixed in 2% paraformaldehyde in 1× PBS for 10 min at RT, and then permeabilized in 0.1% Triton in 1× PBS for 15 min at RT. The permeabilized cell samples were rinsed with PBS again, prior to labeling. For Click-PAINT labeling, the cells were incubated in 15 µM of the docking strand oligonucleotide (5'-ttatacatcta-3', functionalized at the 5' terminus with 1,2,4,5-tetrazine; SEQ ID NO:19) in 1× PBS for 10 min at 37° C., and then rinsed with 1× PBS. Prior to imaging and either on the same day or up to 3 days after cell incubation with the docking strand, the imager strand (5'-ctagatgtat-3', functionalized at the 3' end with Atto655; SEQ ID NO:20) was added to the cells at a final concentration of 800 pM (in 1× PBS, 500 mM NaCl, pH 8, as described in Jungmann et al., Nat Methods 11:313-318, 2014).

(H) Click-PAINT Imaging and Image Processing

Click-PAINT microscopy was performed using a Leica GSD microscope, equipped with a Leica HCX PL APO 160×/NA 1.43 oil CORR TIRF PIFOC objective and GFP, Cy3 and Cy5 filter sets. All images were acquired in the TIRF mode. For vimentin imaging, the Cy3 channel (532 nm excitation) was used to identify transfected cells based on the vimentin-mOrange fusion. Due to the position of mOrange at the C terminus only the cells which successfully incorporated the UAA when expressing vimentin-mOrange contributed to the fluorescence signal. For Nup153, a GFP fusion was used to identify transfected cells. Atto655 was excited with a 642 nm laser and images were acquired with 100 ms exposure in the TIRF mode. For each image, 30,000-100,000 frames were acquired.

Super-resolution Click-PAINT images were reconstructed using the Localizer Package (Dedecker et al., J Biomed Opt 17:126008, 2012) for IgorPro (Wavemetrics, Portland, USA). Firstly, a threshold based on the maximum likelihood ratio was applied, followed by fitting with a symmetrical 2D Gaussian function for localization of the spots. Sporadic long-lasting associations of docking and imager strands were observed, giving rise to repetitive localization in sequential frames. In order to correct for this, identical emitters (falling within one standard deviation of the spot fit) were consolidated into a single intensity-weighed localization. Finally, a super-resolution image was reconstructed from binning all the detected events and convolving the resulting image with a Gaussian width according to the resolution determined by the Fourier ring correlation $2\delta$ criterion for Nup153 and 0.143 criterion for vimentin (Banterle et al., J Struct Biol 183:363-367, 2013).

(I) Baculovirus-Based Transfection of Insect Cells

Following standard protocols, insect cells of line Sf21 were cultured in a protein-free, serum-free standard culture medium for *Spodoptera frugiperda* cells (Sf-900™ III SFM) at 27° C. shaking at 180 rpm. The Sf21 cells were split every day to a density of $0.6 \times 10^6$ cells/ml or every third day to a density of $0.3 \times 10^6$ cells/ml.

Baculovirus shuttle vector (Bacmid) DNA containing an expression cassette encoding tRNA$^{Pyl}$, mCherry-GFP$^{Y39TAG}$ and either PylRS$^{AF}$ or NES-PylRS$^{AF}$ was prepared using standard cloning and recombination procedures.

For transfection 3 ml/well of $0.3 \times 10^6$ Sf21 cells/ml were seeded in a 6-well cell culture multidish (Nunclon Delta Surface, Thermo scientific) and transfected with Bacmid DNA using a nonliposomal transfection reagent (FuGENE®HD Transfection Reagent, Promega) following the manufacturer's instructions. $V_0$-virus was harvested 70 h post transfection and the $V_1$-generation was started. Therefor, 25 ml Sf21 cells at $0.6 \times 10^6$ cells/ml were transfected with 3 ml of the $V_0$-virus. After cell proliferation stopped, the cultures were kept for another 48-60 h at 27° C. shaking at 180 rpm. The transfected cells were harvested by centrifugation (500 rpm, 10 min) and the supernatant (i.e., the $V_1$-Virus) was stored at 4° C.

(J) Expression Experiments Using Transfected Insect Cells 5-25 ml Sf21 cells at $0.6 \times 10^6$ cells/ml were transduced with $V_1$-virus prepared by method (I) at a ratio of 100:1 vol/vol (cells:virus). One day afterwards, different amounts of UAA 1 (0-1 mM final concentration) was added to the cultures. After three days of culture, the cells were harvested by centrifugation (500 rpm, 10 min), cooled down to 4° C., resuspended in 2 ml sterile 1× PBS, filtered through a cell strainer (Falcon, 70 μm, Fisher Scientific) and kept on ice until analysis. Data for 500,000 cells of each sample was acquired and analyzed using a LSRFortessa SORP Cell Analyzer (Becton, Dickinson and Company) and the FlowJo software (FlowJo Enterprise). Cells were gated first by cell type (using FSC-A×SSC-A parameters) and then by single cell (FSC-A×SSC-W). GFP fluorescence was acquired in the 488-530/30 channel and mCherry fluorescence in the 561-610/20 channel.

Example 1

Identification of Putative NLS in *M. mazei* and *M. barkeri* PylRS

Computational analysis of the amino acid sequences of *M. mazei* PylRS and *M. barkeri* PylRS (shown below) predicted a putative nuclear localization sequence (NLS, under-lined portion of the PylRS sequences shown below).

```
                                                          SEQ ID NO: 1
MDKKPLNTLISATGLWMSRTGTIHKIKHHEVSRSKIYIEMACGDHLVVNNSRSSRTARAL    60

RHHKYRKTCKRCRVSDEDLNKFLTKANEDQTSVKVKVVSAPTRTKKAMPKSVARAPKPLE  120

NTEAAQAQPSGSKFSPAIPVSTQESVSVPASVSTSISSISTGATASALVKGNTNPITSMS  180

APVQASAPALTKSQTDRLEVLLNPKDEISLNSGKPFRELESELLSRRKKDLQQIYAEERE  240

NYLGKLEREITRFFVDRGFLEIKSPILIPLEYIERMGIDNDTELSKQIFRVDKNFCLRPM  300

LAPNLYNYLRKLDRALPDPIKIFEIGPCYRKESDGKEHLEEFTMLNFCQMGSGCTRENLE  360

SIITDFLNHLGIDFKIVGDSCMVYGDILDVMHGDLELSSAVVGPIPLDREWGIDKPWIGA  420

GFGLERLLKVKHDFKNIKRAARSESYYNGISTNL                            454

SEQ ID NO: 3
MDKKPLDVLISATGLWMSRTGILHKIKHHEVSRSKIYIEMACGDHLVVNNSRSCRTARAF    60

RHHKYRKTCKRCRVSDEDINNFLIRSTESKNSVKVRVVSAPKVKKAMPKSVSRAPKPLEN  120

SVSAKASINTSRSVPSPAKSTPNSSVPASAPAPSLIRSQLDRVEALLSPEDKISLNMAKP  180

FRELEPELVIRRKNDFQRLYINDREDYLGKLERDITKFFVDRGFLEIKSPILIPAEYVER  240

MGINNDTELSKQIFRVDKNLCLRPMLAPTLYNYLRKLDRILPGPIKIFEVGPCYRKESDG  300

KEHLEEFTMVNFCQMGSGCTRENLEALIKEFLDYLEIDFEIVGDSCMVYGDILDIMHGDL  360

ELSSAVVGPVSLDREWGIDKPWIGAGFGLERLLKVMHGFKNIKRASRSESYYNGISTNL   419
```

The NLS motifs were predicted using "cNLS Mapper" (Kosugi et al., Proc Natl Acad Sci USA 106:10171-10176, 2009).

Example 2

Intracellular Localization of M. mazei PylRS$^{AF}$

In examples 2-5, M. mazei PylRS$^{AF}$ was used (therein referred to simply as "PylRS$^{AF}$").

HEK293T cells and COS-7 cells were transfected with a plasmid facilitating eukaryotic expression of tRNA$^{Pyl}$/PylRS$^{AF}$ (pcDNA3.1 tRNA$^{Pyl}$/PylRS$^{AF}$) and immunostained with polyclonal anti-PylRS antibody or tRNA$^{Pyl}$ was detected by FISH using methods (B) and (E) described herein.

As shown in FIGS. 1a, 2a, 3a and 4a, for both HEK293T and COS-7 cells, strong nuclear and putatively nucleolar immunostaining and FISH signals were detected, while there was almost no signal in the cytoplasm. This indicates that PylRS$^{AF}$ and tRNA$^{Pyl}$ were localized predominantly in the nucleus rather than in the cytoplasm, where translation takes place.

Example 3

Amber Suppression by PylRS$^{AF}$ and NES-PylRS$^{AF}$

A PylRS$^{AF}$ variant was prepared which differs from PylRS$^{AF}$ (amino acid sequence set forth in SEQ ID NO:2) in having a strong N-terminal NES ("NES-PylRS$^{AF}$", amino acid sequence set forth in SEQ ID NO:12).

HEK293T cells were co-transfected with polynucleotides encoding tRNA$^{Pyl}$, iRFP-GFP$^{Y39TAG}$ and either PylRS$^{AF}$ or NES-PylRS$^{AF}$ using method (B) described herein. HEK293T cells expressing iRFP-GFP$^{Y39TAG}$ in the presence or absence of 1 (BOC) were analyzed for GFP and iRFP fluorescence using flow cytometry method (D) described herein 2 days post-transfection.

iRFP-GFP$^{Y39TAG}$ is a fusion of iRFP (infrared fluorescent protein) and GFP (green fluorescent protein), wherein the permissive site 39 of GFP is encoded by the amber (TAG) stop codon. iRFP-GFP$^{Y39TAG}$ serves as an amber suppression reporter because the cells turn red (express iRFP) if properly transfected but GFP is only produced if the amber codon is suppressed to encode the UAA (here: BOC). The ratio of green fluorescence (GFP) to red fluorescence (iRFP) in the cells is therefore an indicator of amber suppression efficiency.

Figure 5:
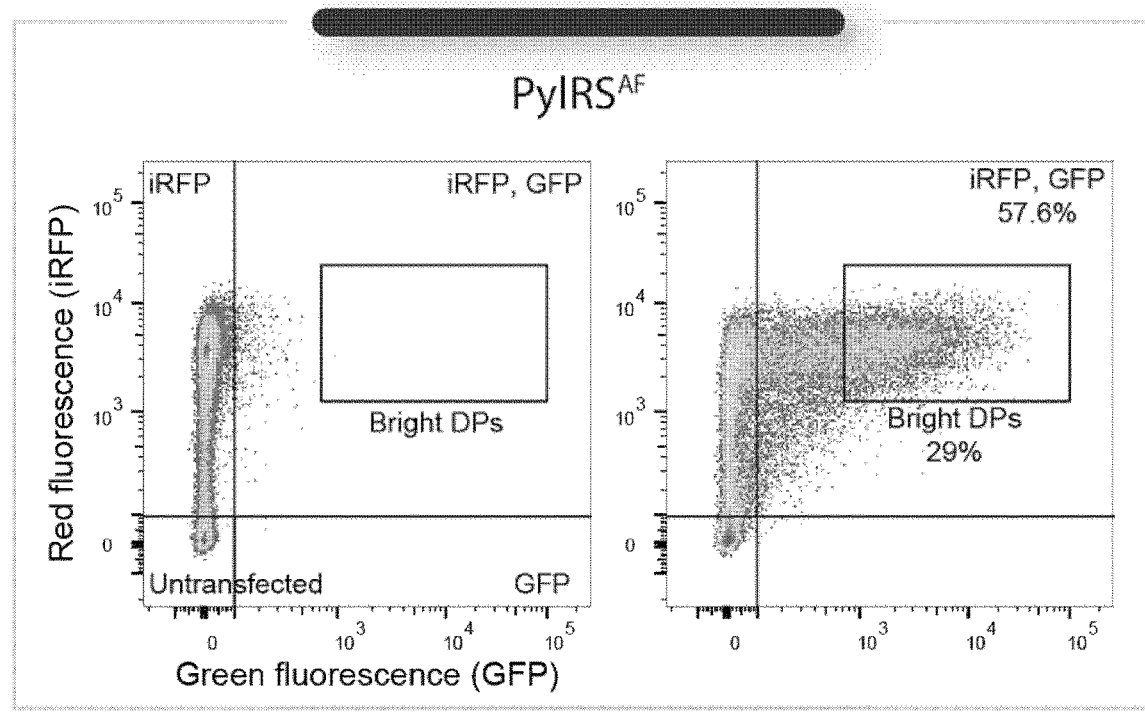
FIG. 5 shows the results of a flow cytometry analysis of HEK293T cells cotransfected with the iRFP-GFP$^{Y39TAG}$ amber suppression reporter and one of the amber suppression pairs: tRNA$^{Pyl}$/PylRS$^{AF}$ and tRNA$^{Pyl}$/NES-PylRS$^{AF}$. For each amber suppression pair, a transfected sample without an UAA (left) and with added BOC (right) is shown. The percentage of amber suppressing cells (gate "iRFP, GFP") is calculated based on the total transfected population (sum of cells in gates "iRFP", "iRFP,GFP" and GFP"). An additional gate with the percentage of bright double positive cells ("Bright DPs") is also shown.
Figure 5:
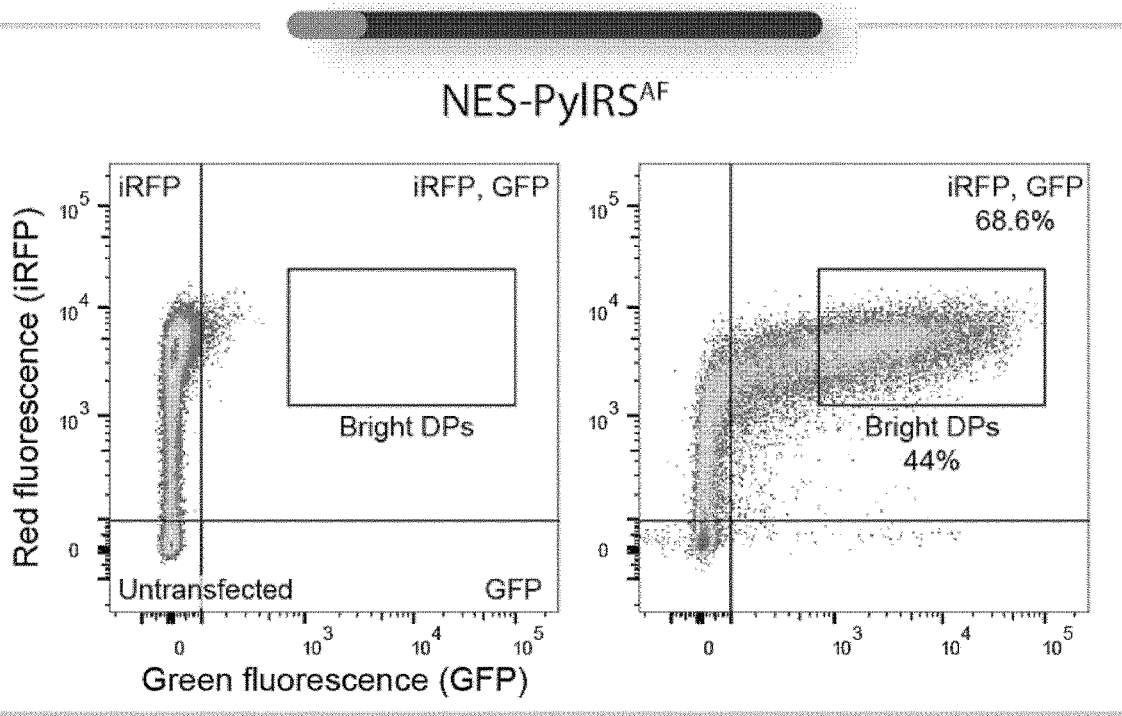

As shown in FIG. 5, NES-PylRS$^{AF}$ showed significant enhancement of amber suppression efficiency (68.6%) compared to PylRS$^{AF}$. The differences in efficiency drop were especially noticeable by inspecting the "Bright DPs" (double positive) population.

Figure 6:
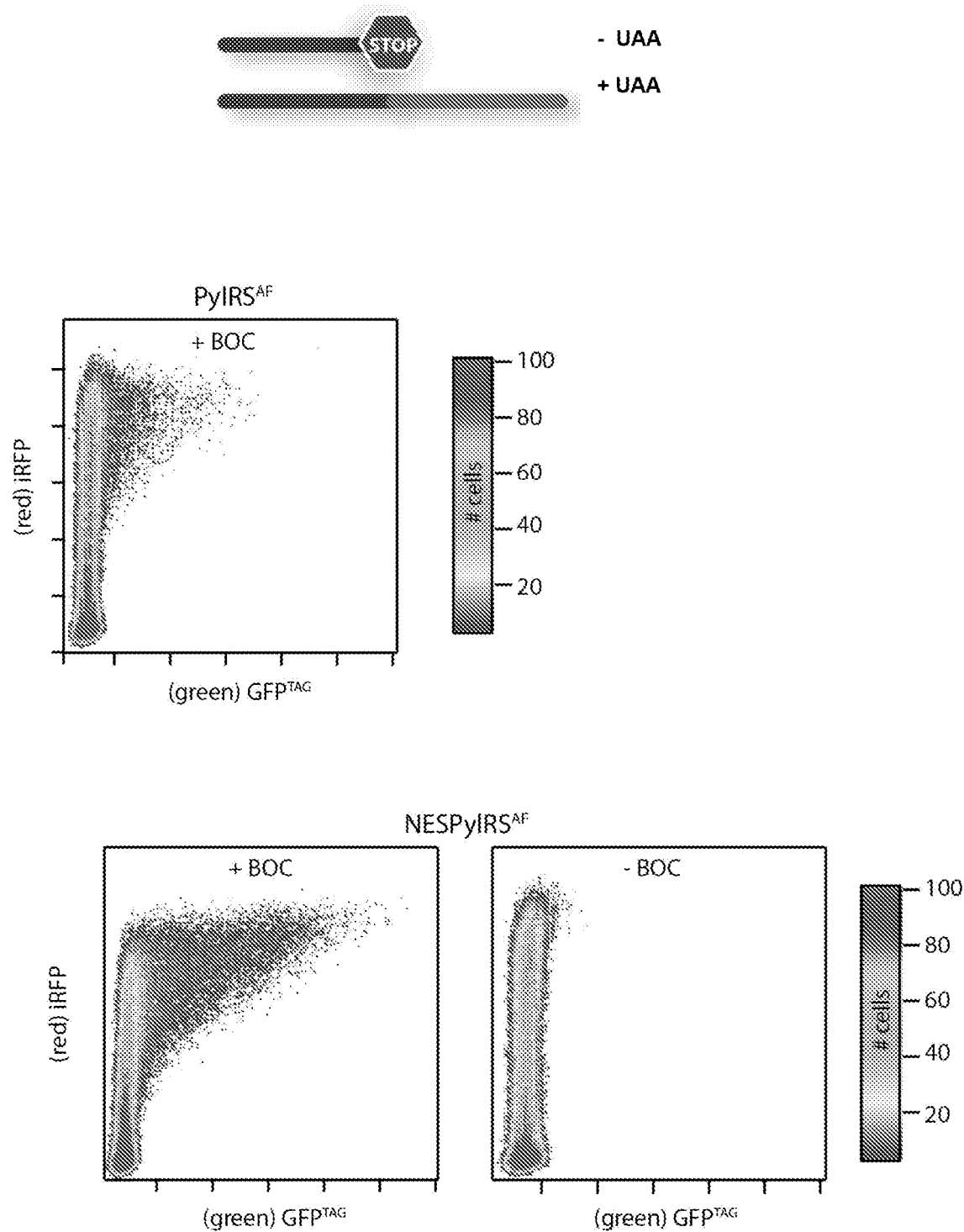
FIG. 6 shows the results of a flow cytometry analysis of HEK293T cells co-transfected with the iRFP-GFP$^{Y39TAG}$ amber suppression reporter and either tRNA$^{Pyl}$/PylRS$^{AF}$ or tRNA$^{Pyl}$/NES-PylRS$^{AF}$ to assess the amber suppression efficiency of PylRS$^{AF}$ in the presence of UAA 1 (left), and the amber suppression efficiency of NES-PylRS$^{AF}$ in the presence of UAA 1 (center) or in the absence of an UAA (right).
Figure 7:
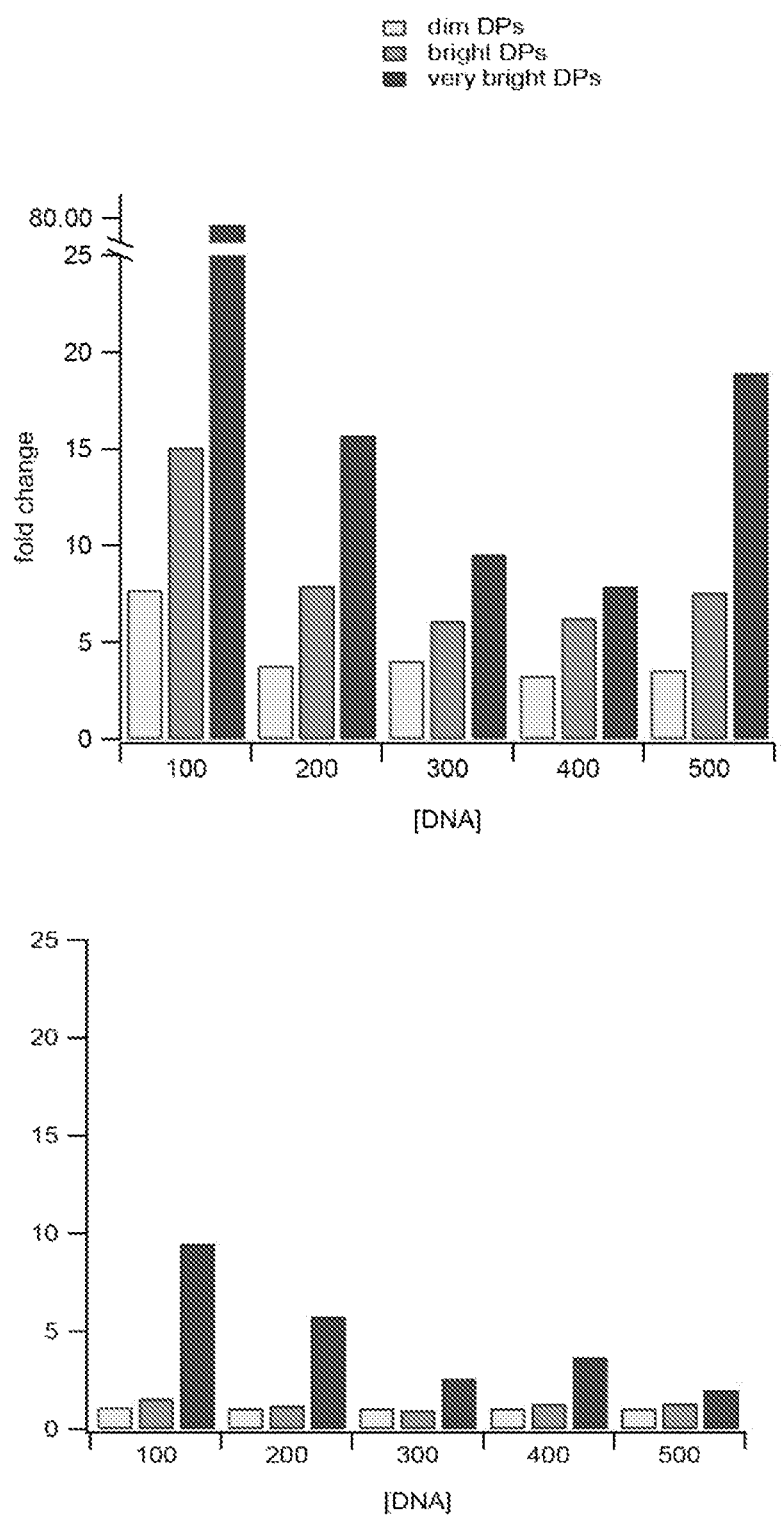
FIG. 7 summarizes the change in the number of GFP fluorescent HEK293T cells (categorized as "dim DPs", "bright DPs" and "very bright DPs") as observed by flow cytometry in cell samples co-transfected with varying amounts of the amber suppression reporter iRFP-GFP$^{Y39TAG}$ (ranging from 100-500 ng plasmid DNA per well) and either tRNA$^{Pyl}$/PylRS$^{AF}$ (reference) or tRNA$^{Pyl}$/NES-PylRS$^{AF}$, and cultured in the presence of a low concentration (50 μM, left graph) or high concentration (250 μM, right graph) of UAA 1. See also example 3.

Additional experiments were performed where HEK293T cells were co-transfected with varying amounts of iRFP-GFP$^{Y39TAG}$ (ranging from 100 to 500 ng plasmid per well) and either tRNA$^{Pyl}$/PylRS$^{AF}$ or tRNA$^{Pyl}$/NES-PylRS$^{AF}$ using method (B) described herein, and low (50 μM) or high (250 μM) concentrations of UAA (BOC) were used. Flow cytometric analysis of these cells using method (D) described herein confirmed that amber suppression efficiency of variant NES-PylRS$^{AF}$ was significantly enhanced compared to PylRS$^{AF}$ (see FIGS. 6 and 7). The number of bright GFP-fluorescent cells (i.e., successful iRFP-GFP$^{Y39TAG}$ amber suppression) observed cell samples transfected with NES-PylRS$^{AF}$ and cultured in the presence of 1 was enhanced up to 15-fold compared to the corresponding cell sample transfected with PylRS$^{AF}$ and cultured in the presence of 1.

Example 4

Intracellular Localization of NES-PylRS$^{AF}$

HEK293T cells and COS-7 cells were transfected with a plasmid facilitating eukaryotic expression of tRNA$^{Pyl}$/NES-PylRS$^{AF}$ and immunostained with polyclonal anti-PylRS antibody or tRNA$^{Pyl}$ was detected by FISH using methods (B) and (E) described herein.

As shown in FIGS. 1b, 2b, 3b and 4b, for both HEK293T and COS-7 cells, clear cytosolic immunostaining and FISH signals were detected, while the strong fluorescence in the nucleus observed with PylRS$^{AF}$ (cf. example 2) was absent. This indicates a cytosolic distribution of NES-PylRS$^{AF}$ and tRNA$^{Pyl}$.

Example 5

Use of NES-PylRS$^{AF}$ in Super-Resolution Microscopy

The new tRNA$^{Pyl}$/NES-PylRS$^{AF}$ amber suppression pair was used for examining distribution of a target polypeptide within transfected HEK293T cells by in super-resolution microscopy using a method termed Click-PAINT that uses elements of the DNA-PAINT microscopy methods described, e.g., by Jungmann et al. (Nat Methods 11:313-318, 2014)

Figure 8:
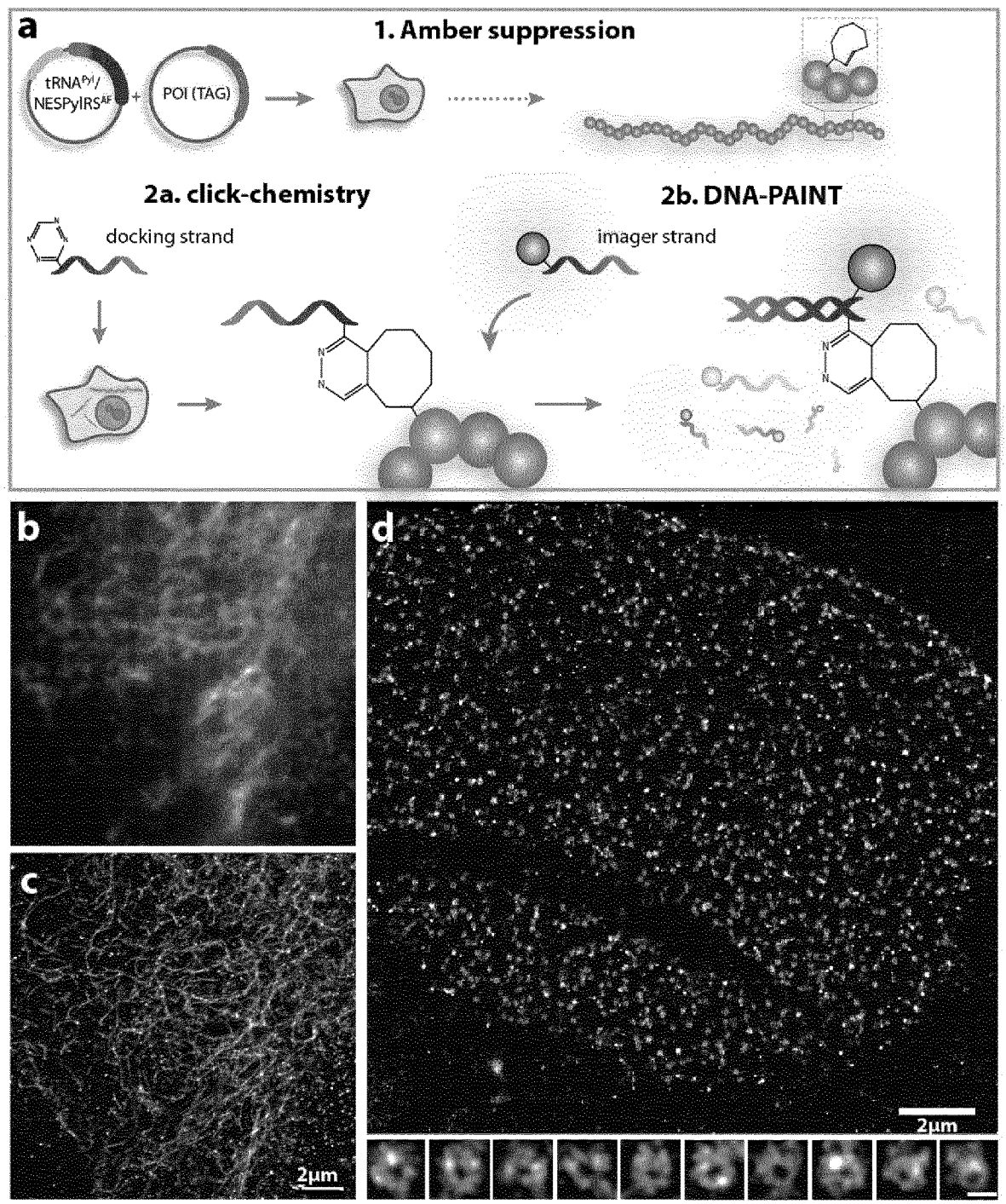
FIG. 8 further shows the fluorescence signal of the fused mOrange protein for the vimentin$^{N116 \rightarrow 2}$-mOrange construct used as a control for protein expression in HEK293T cells cotransfected with pVimentin$^{N116TAG}$-mOrange and tRNA$^{Pyl}$/NES-PylRS$^{AF}$ (b); DNA-PAINT-based SRM of HEK293T cells cotransfected with tRNA$^{Pyl}$/NES-PylRS$^{AF}$ and either pVimentin$^{N116TAG}$-mOrange (c) or pGFP$^{N149TAG}$-Nup153 (d) and expressing a vimentin-mOrange fusion (c) or GFP-Nup153 fusion (d) with UAA 2 incorporated at the amber encoded position, wherein the fusion proteins are labeled at the UAA 2-derived amino acid reside using the Click-PAINT protocol described herein (scale bar in zoomed images of nuclear pores is 100 nm).

The principle of Click-PAINT is outlined in FIG. 8a. The cells express a target polypeptide (POI) comprising an UAA residue. The UAA residue comprises a labeling group (e.g., a trans-cyclooctenyl group). The cell is contacted with a docking strand oligonucleotide carrying a docking group (e.g., a 1,2,4,5-tetrazine group) that reacts via Click reaction (such as SPAAC or SPIEDAC) with the labeling group of the UAA residue, thus coupling the docking strand to the POI. Then, an imager strand carrying an imaging group (for example a dye such as Atto655) is added to the cells. Proper choice of the location of the docking group within the docking strand oligonucleotide (e.g., at the 5' end) and the location of the imaging group within the imager strand (e.g., at the 3' end) allow for the imaging group being located in direct proximity to the labeling site (UUA residue) of the labeled POI upon annealing of the imager strand with the POI-bound docking strand.

The new Click-PAINT method was tested with two POIs.

Cytoskeletal elements are an ideal starting point to validate SRM techniques as they result in defined filamentous patterns and the filament is highly enriched in individual proteins. The first POI (Vimentin$^{N116TAG}$-mOrange) was therefore a fusion protein comprising at the N-terminus a mutant of cytoskeletal protein vimentin, wherein N116 was replaced by an amber codon (vimentin$^{N116TAG}$) and at the C-terminus mOrange. The mOrange serves as a reference to check for specificity of the labeling using conventional wide-field microscopy.

To test the sensitivity of the new Click-PAINT method, the second POI (GFP$^{N149TAG}$-Nup153) was a protein of the nuclear pore complex, a much less abundant structure than the cytoskeleton. The nuclear pore complex is a ring-like structure built from about 30 different proteins and comprising 32 copies of the protein Nup153 which has an approximate size of 60 nm$^3$. Thus, the density of potential labeling sites on Nup 153 is substantially lower than the density of potential labeling sites on cytoskeletal filaments. Specifically, the second pOI was a fusion protein comprising at the N-terminus mutated GFP, wherein N149 was replaced by an amber codon ($GFP^{N149TAG}$) and at the C-terminus Nup153.

Constructs for the expression of the target polypeptides were prepared, HEK293T cells were co-transfected with polynucleotides encoding $tRNA^{Pyl}$/NES-$PylRS^{AF}$ and either $Vimentin^{N116TAG}$-mOrange or $GFP^{N149TAG}$-Nup153, and the transfected cells were cultured in UAA 2 using method (F) described herein. Click-PAINT labeling, imaging and image processing were carried out using methods (G) and (H) described herein.

FIG. 8c shows an SRM image generated using the Click-PAINT method described above and $Vimentin^{N116TAG}$-mOrange. Said image has a resolution that is clearly enhances compared to the diffraction-limited imaging of the mOrange reference channel (see FIG. 8b).

Using $GFP^{N149TAG}$-Nup153 as POI, the Click-PAINT method generated high-contrast, super-resolved images showing the typical circular appearance of nuclear pore complexes (see FIG. 8d). Not all observed ring structures were closed because the cells also expressed wild-type Nup153 which cannot be labeled and competes for incorporation into the nuclear core complexes with the $GFP^{N149 \rightarrow 2}$-Nup153 protein.

Example 6

Amber Suppression by $PylRS^{AF}$ and NES-$PylRS^{AF}$ in Baculovirus-Based Insect Cell Protein Expression Sf21 cells were transduced with Bacmid DNA encoding $tRNA^{Pyl}$, mCherry-$GFP^{Y39TAG}$, and either $PylRS^{AF}$ or NES-$PylRS^{AF}$, cultured with different concentrations (0, 10, 50, 100, 250, 500 or 1000 μM) of UAA 1 (BOC) and analyzed using methods (I) and (J) described herein.

mCherry fluorescence of the cells indicated successful transduction with Bacmid DNA. GFP fluorescence of the cells indicated successful suppression of the amber stop codon encoding amino acid position 39 of the $GFP^{Y39TAG}$ reporter gene by incorporation of UAA 1 at said position.

Figure 9:
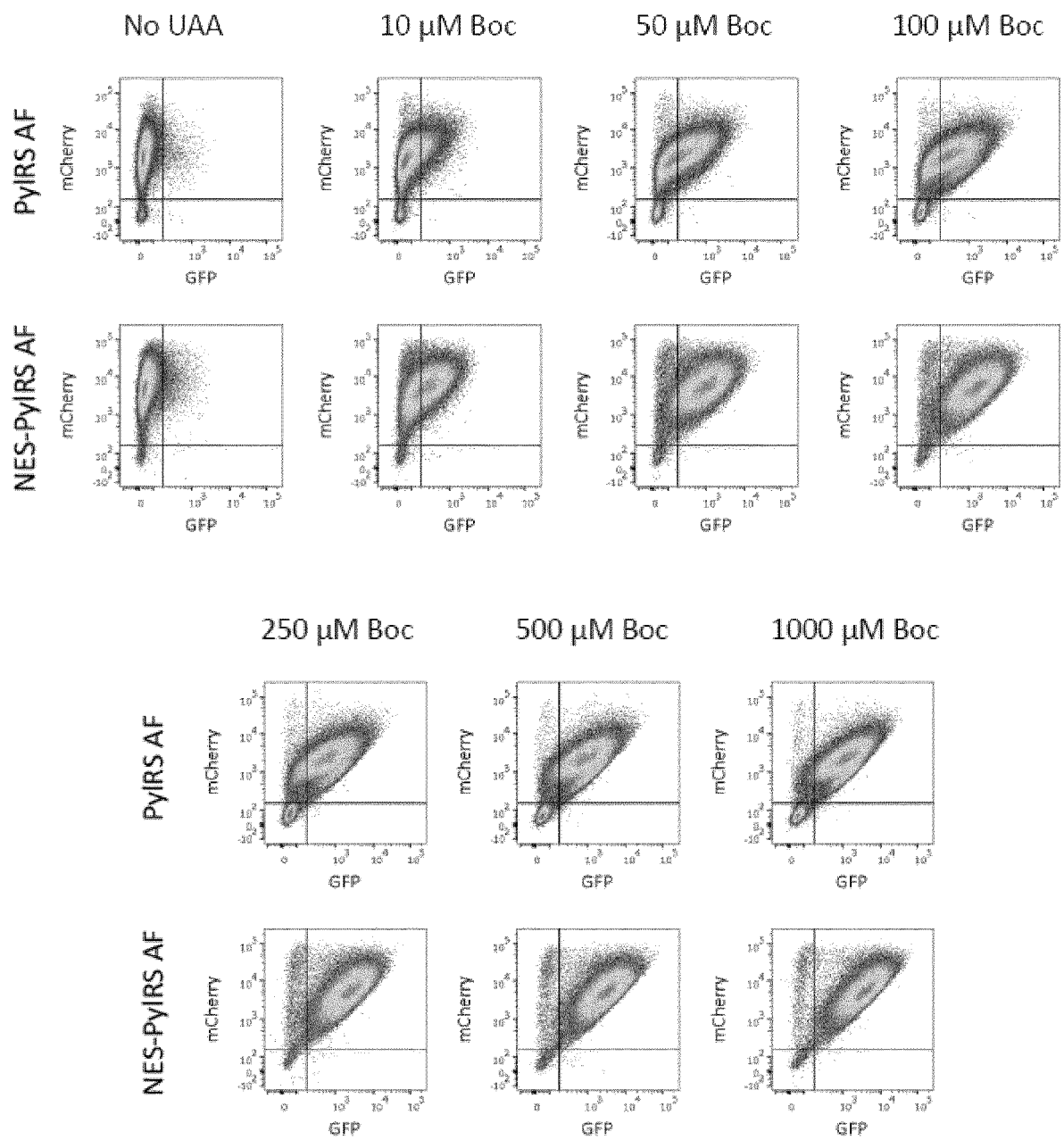
FIG. 9 shows the results of a flow cytometry analysis of Sf21 cells co-transfected with the mCherry-GFP$^{Y39TAG}$ amber suppression reporter and one of the amber suppression pairs: tRNA$^{Pyl}$/PylRS$^{AF}$ or tRNA$^{Pyl}$/NES-PylRS$^{AF}$. For each amber suppression pair transfected samples without UAA and with different concentrations of added UAA 1 are shown. Each dot plot is divided into four sections: the upper left section shows "mCherry only" cells which expressed mCherry (i.e. were successfully transfected) but not GFP (i.e. were unable to suppress the amber stop codon in GFP$^{Y39TAG}$); the upper right section shows "double positives" cells which expressed both mCherry and GFP (i.e. which successfully incorporated UAA 1 into GFP); and the lower left section shows "double negatives" cells (i.e. which were not successfully transfected). See also example 6.
Figure 10:
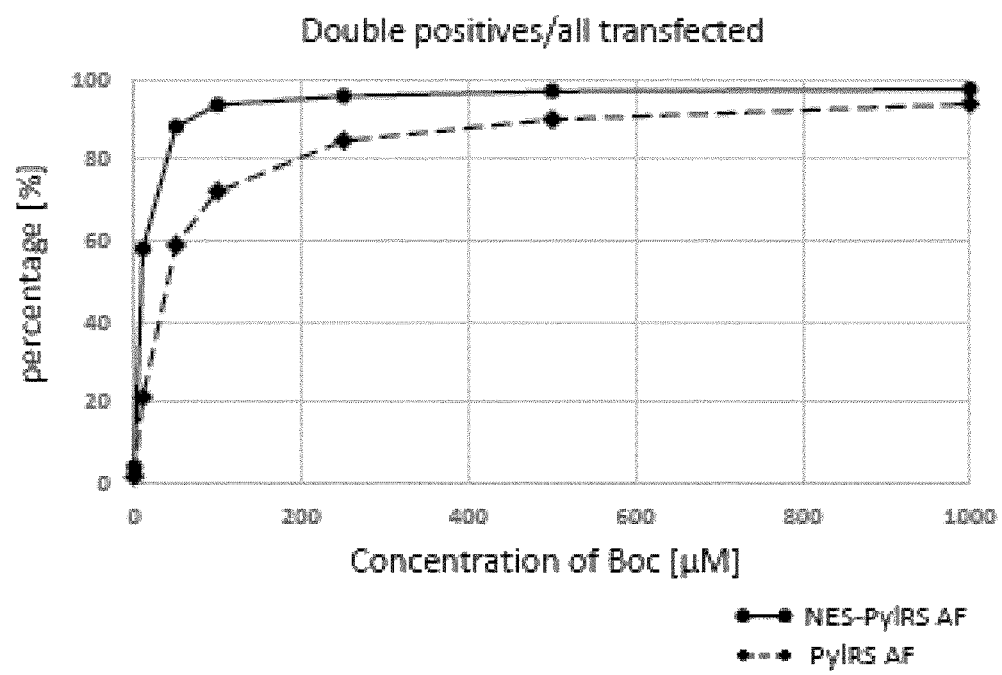
FIG. 10 shows the percentage of "double positives" relative to the total number of transfected cells, for the different UAA 1 concentrations in the Sf21 cell samples depicted in FIG. 9. See also example 6.
Figure 11:
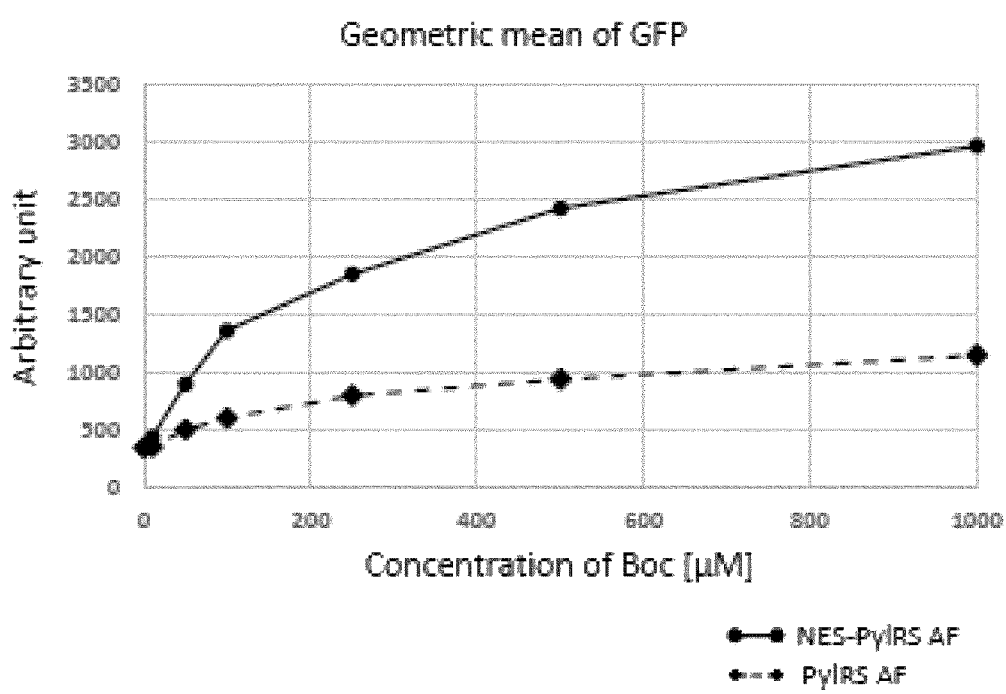
FIG. 11 shows the geometric mean of the GFP signal in the "double positives" for the different UAA 1 concentrations in the Sf21 cell samples depicted in FIG. 9. See also example 6.

Flow cytometric analysis showed an UAA 1-dose-dependent increase of mCherry- and GFP-fluorescent ("double positive") cells for both $PylRS^{AF}$ and NES-$PylRS^{AF}$ where the increase for NES-$PylRS^{AF}$-expressing cells was significantly more pronounced than in $PylRS^{AF}$-expressing cells, indicating that NES-$PylRS^{AF}$ allowed for higher efficiency than $PylRS^{AF}$ even at lower UAA 1 concentrations. See FIGS. 9, 10 and 11, and Table 1.

TABLE 1

Relative size of fluorescent cell sub-populations in Sf21 cells transduced with Bacmid DNA encoding $tRNA^{Pyl}$, mCherry, $GFP^{Y39TAG}$ and either $PylRS^{AF}$ or NES-$PylRS^{AF}$ and incubated with different UAA 1 concentrations

| PylRS | UAA 1 conc. [μM] | Cells showing only mCherry fluorescence [%] | Cells showing both mCherry and GFP fluorescence [%] |
|---|---|---|---|
| $PylRS^{AF}$ | 0 | 94.6 | 1.4 |
| | 10 | 75.8 | 20.1 |
| | 50 | 39.3 | 56.2 |
| | 100 | 25.9 | 67.1 |
| | 250 | 13.9 | 76.5 |
| | 500 | 9.1 | 81.6 |
| | 1000 | 5.7 | 85.8 |
| NES-$PylRS^{AF}$ | 0 | 95.1 | 3.7 |
| | 10 | 41.6 | 57.0 |
| | 50 | 11.7 | 86.9 |
| | 100 | 6.3 | 92.2 |
| | 250 | 4.2 | 94.6 |
| | 500 | 2.9 | 95.5 |
| | 1000 | 2.5 | 96.3 |

ABBREVIATIONS

RS=aminoacyl tRNA synthetase
BOC=Boc-L-Lys-OH=N-α-tert-butyloxycarbonyl-L-lysine (FIG. 1a, compound 1)
Crm1=chromosomal region maintenance 1, also known as karyopherin exportin 1
dSTORM=direct stochastic optical reconstruction microscopy
*E. coli* BL21(DE3)AI=*E. coli* strain B F⁻ ompT gal dcm Ion $hsdS_B(r_B^- m_B^-)\lambda$(DE3 [lacI lacUV5-T7p07 ind1 sam7 nin5])[malB⁺]$_{K-12}$($\lambda A^S$) araB:T7RNAP-tetA
FBS=fetal bovine serum
FISH=fluorescence in situ hybridization
GFP=green fluorescent protein
Hoechst 33342=2'-(4-Ethoxyphenyl)-5-(4-methyl-1-piperazinyl)-2,5'-bi-1H-benzimidazole trihydrochloride
IPTG=isopropyl β-D-1-thiogalactopyranoside
iRFP=infrared fluorescent protein
NES=nuclear export signal
NLS=nuclear localization signal
PBS=phosphate buffered saline
PAINT=point accumulation for imaging in nanoscale topography
PylRS=pyrrolysyl tRNA synthetase
$PylRS^{AF}$=mutant *M. mazei* pyrrolysyl tRNA synthetase comprising amino acid substitutions Y306A and Y384F
PMSF=phenylmethylsulfonyl fluoride
POI=polypeptide of interest, target polypeptide
RP-HPLC=reversed phase high-performance liquid chromatography
RT=room temperature
TCEP=tris(2-carboxyethyl)phosphine
TEV=*Tobacco Etch Virus* nuclear-inclusion-a endopeptidase
$tRNA^{Pyl}$=tRNA that is acylated by a wild-type or modified PylRS and has an anticodon that, for site-specific incorporation of the UAA into a POI, is preferably the reverse complement of a selector codon. (In the $tRNA^{Pyl}$ used in the examples, the anticodon is CUA.)
SPAAC=(copper-free) strain promoted alkyne-azide cycloaddition
SPIEDAC=(copper-free) strain promoted inverse-electron-demand Diels-Alder cycloaddition
SRM=super-resolution microscopy
TB=Terrific Broth
TCO*=N-ε-((trans-cyclooct-2-en-1-yloxy)carbonyl)-L-lysine (FIG. 1a, compound 2)
UAA=unnatural amino acid

The invention claimed is:

1. A modified *Methanosarcina mazei* pyrrolysyl tRNA synthetase sequence or a *Methanosarcina barkeri* pyrrolysyl tRNA synthetase sequence wherein the modified pyrrolysyl tRNA synthetases are modified by introduction of a nuclear export signal, while retaining pyrrolysyl tRNA synthetase activity.

2. The modified archaeal pyrrolysyl tRNA synthetase of claim 1, which comprises a nuclear export signal, and lacks a nuclear localization signal.

3. The pyrrolysyl tRNA synthetase of claim 1, wherein the nuclear export signal comprises the amino acid sequence set forth in SEQ ID NO:4 or the amino acid sequence set forth in SEQ ID NO:5.

4. The pyrrolysyl tRNA synthetase of claim 1, wherein the nuclear export signal comprises an amino acid sequence selected from the sequences set forth in SEQ ID NOs:6-9.

5. The pyrrolysyl tRNA synthetase of claim 1, wherein the pyrrolysyl tRNA synthetase comprises a *Methanosarcina mazei* pyrrolysyl tRNA synthetase of SEQ ID NO:1 or 2, a *Methanosarcina barkeri* pyrrolysyl tRNA synthetase of SEQ ID NO: 3, or a sequence having at least 90% sequence identity to any one of the sequences of SEQ ID NO: 1, 2 or 3.

* * * * *

SEQUENCE LISTING

<160> NUMBER OF SEQ ID NOS: 20

<210> SEQ ID NO 1
<211> LENGTH: 454
<212> TYPE: PRT
<213> ORGANISM: Methanosarcina mazei

<400> SEQUENCE: 1

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365
```

```
His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Glu Ser Tyr Tyr Asn
                435                 440                 445

Gly Ile Ser Thr Asn Leu
        450

<210> SEQ ID NO 2
<211> LENGTH: 454
<212> TYPE: PRT
<213> ORGANISM: Artificial Sequence
<220> FEATURE:
<223> OTHER INFORMATION: Methanosarcina mazei PylRS Y306A, Y384F mutant
<220> FEATURE:
<221> NAME/KEY: MUTAGEN
<222> LOCATION: 306
<223> OTHER INFORMATION: Y306A mutation
<220> FEATURE:
<221> NAME/KEY: MUTAGEN
<222> LOCATION: 384
<223> OTHER INFORMATION: Y384F mutation

<400> SEQUENCE: 2

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
                100                 105                 110

Ala Arg Ala Pro Lys Pro Leu Glu Asn Thr Glu Ala Ala Gln Ala Gln
            115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
                180                 185                 190

Ser Gln Thr Asp Arg Leu Glu Val Leu Leu Asn Pro Lys Asp Glu Ile
            195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
```

```
            225                 230                 235                 240
Asn Tyr Leu Gly Lys Leu Glu Arg Glu Ile Thr Arg Phe Phe Val Asp
                    245                 250                 255

Arg Gly Phe Leu Glu Ile Lys Ser Pro Ile Leu Ile Pro Leu Glu Tyr
                    260                 265                 270

Ile Glu Arg Met Gly Ile Asp Asn Asp Thr Glu Leu Ser Lys Gln Ile
                    275                 280                 285

Phe Arg Val Asp Lys Asn Phe Cys Leu Arg Pro Met Leu Ala Pro Asn
                    290                 295                 300

Leu Ala Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                    325                 330                 335

Glu His Leu Glu Glu Phe Thr Met Leu Asn Phe Cys Gln Met Gly Ser
                    340                 345                 350

Gly Cys Thr Arg Glu Asn Leu Glu Ser Ile Ile Thr Asp Phe Leu Asn
                    355                 360                 365

His Leu Gly Ile Asp Phe Lys Ile Val Gly Asp Ser Cys Met Val Phe
                    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                    405                 410                 415

Trp Ile Gly Ala Gly Phe Gly Leu Glu Arg Leu Leu Lys Val Lys His
                    420                 425                 430

Asp Phe Lys Asn Ile Lys Arg Ala Ala Arg Ser Glu Ser Tyr Tyr Asn
                    435                 440                 445

Gly Ile Ser Thr Asn Leu
        450

<210> SEQ ID NO 3
<211> LENGTH: 419
<212> TYPE: PRT
<213> ORGANISM: Methanosarcina barkeri

<400> SEQUENCE: 3

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                    20                  25                  30

Arg Ser Lys Ile Tyr Ile Glu Met Ala Cys Gly Asp His Leu Val Val
                    35                  40                  45

Asn Asn Ser Arg Ser Cys Arg Thr Ala Arg Ala Phe Arg His His Lys
            50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                    85                  90                  95

Val Val Ser Ala Pro Lys Val Lys Lys Ala Met Pro Lys Ser Val Ser
                    100                 105                 110

Arg Ala Pro Lys Pro Leu Glu Asn Ser Val Ser Ala Lys Ala Ser Thr
                    115                 120                 125

Asn Thr Ser Arg Ser Val Pro Ser Pro Ala Lys Ser Thr Pro Asn Ser
            130                 135                 140
```

```
Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 4
<211> LENGTH: 6
<212> TYPE: PRT
<213> ORGANISM: Artificial Sequence
<220> FEATURE:
<223> OTHER INFORMATION: NES motif
<220> FEATURE:
<221> NAME/KEY: VARIANT
<222> LOCATION: 1,4,6
<223> OTHER INFORMATION: independently selected from Leu, Ile, Val, Phe
      and Met
<220> FEATURE:
<221> NAME/KEY: VARIANT
<222> LOCATION: 2,3,5
<223> OTHER INFORMATION: independently selected from any amino acid

<400> SEQUENCE: 4

Xaa Xaa Xaa Xaa Xaa Xaa
1               5

<210> SEQ ID NO 5
<211> LENGTH: 7
<212> TYPE: PRT
```

```
<213> ORGANISM: Artificial Sequence
<220> FEATURE:
<223> OTHER INFORMATION: NES motif
<220> FEATURE:
<221> NAME/KEY: VARIANT
<222> LOCATION: 1,5,7
<223> OTHER INFORMATION: independently selected from Leu, Ile, Val, Phe
      and Met
<220> FEATURE:
<221> NAME/KEY: VARIANT
<222> LOCATION: 2,3,4,6
<223> OTHER INFORMATION: independently selected from any amino acid

<400> SEQUENCE: 5

Xaa Xaa Xaa Xaa Xaa Xaa Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: NES motif
<220> FEATURE:
<221> NAME/KEY: VARIANT
<222> LOCATION: 1,7
<223> OTHER INFORMATION: Leu
<220> FEATURE:
<221> NAME/KEY: VARIANT
<222> LOCATION: 2,3,5,6,8
<223> OTHER INFORMATION: independently selected from any amino acid
<220> FEATURE:
<221> NAME/KEY: VARIANT
<222> LOCATION: 4
<223> OTHER INFORMATION: independently selected from Leu, Ile, Val, Phe
      and Met
<220> FEATURE:
<221> NAME/KEY: VARIANT
<222> LOCATION: 9
<223> OTHER INFORMATION: independently selected from Leu and Ile

<400> SEQUENCE: 6

Xaa Xaa Xaa Xaa Xaa Xaa Xaa Xaa Xaa
1               5

<210> SEQ ID NO 7
<211> LENGTH: 10
<212> TYPE: PRT
<213> ORGANISM: Artificial Sequence
<220> FEATURE:
<223> OTHER INFORMATION: NES motif
<220> FEATURE:
<221> NAME/KEY: VARIANT
<222> LOCATION: 1,8
<223> OTHER INFORMATION: Leu
<220> FEATURE:
<221> NAME/KEY: VARIANT
<222> LOCATION: 2,3,4,6,7,9
<223> OTHER INFORMATION: independently selected from any amino acid
<220> FEATURE:
<221> NAME/KEY: VARIANT
<222> LOCATION: 5
<223> OTHER INFORMATION: independently selected from Leu, Ile, Val, Phe
      and Met
<220> FEATURE:
<221> NAME/KEY: VARIANT
<222> LOCATION: 10
<223> OTHER INFORMATION: independently selected from Leu and Ile

<400> SEQUENCE: 7

Xaa Xaa Xaa Xaa Xaa Xaa Xaa Xaa Xaa Xaa
1               5                   10
```

-continued

```
<210> SEQ ID NO 8
<211> LENGTH: 10
<212> TYPE: PRT
<213> ORGANISM: Artificial Sequence
<220> FEATURE:
<223> OTHER INFORMATION: NES motif
<220> FEATURE:
<221> NAME/KEY: VARIANT
<222> LOCATION: 1,8
<223> OTHER INFORMATION: Leu
<220> FEATURE:
<221> NAME/KEY: VARIANT
<222> LOCATION: 2,3,5,6,7,9
<223> OTHER INFORMATION: independently selected from any amino acid
<220> FEATURE:
<221> NAME/KEY: VARIANT
<222> LOCATION: 4
<223> OTHER INFORMATION: independently selected from Leu, Ile, Val, Phe
      and Met
<220> FEATURE:
<221> NAME/KEY: VARIANT
<222> LOCATION: 10
<223> OTHER INFORMATION: independently selected from Leu and Ile

<400> SEQUENCE: 8

Xaa Xaa Xaa Xaa Xaa Xaa Xaa Xaa Xaa Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: NES motif
<220> FEATURE:
<221> NAME/KEY: VARIANT
<222> LOCATION: 1,9
<223> OTHER INFORMATION: Leu
<220> FEATURE:
<221> NAME/KEY: VARIANT
<222> LOCATION: 2,3,4,6,7,8,10
<223> OTHER INFORMATION: independently selected from any amino acid
<220> FEATURE:
<221> NAME/KEY: VARIANT
<222> LOCATION: 5
<223> OTHER INFORMATION: independently selected from Leu, Ile, Val, Phe
      and Met
<220> FEATURE:
<221> NAME/KEY: VARIANT
<222> LOCATION: 11
<223> OTHER INFORMATION: independently selected from Leu and Ile

<400> SEQUENCE: 9

Xaa Xaa Xaa Xaa Xaa Xaa Xaa Xaa Xaa Xaa Xaa
1               5                   10

<210> SEQ ID NO 10
<211> LENGTH: 9
<212> TYPE: PRT
<213> ORGANISM: Artificial Sequence
<220> FEATURE:
<223> OTHER INFORMATION: NES motif

<400> SEQUENCE: 10

Leu Pro Pro Leu Glu Arg Leu Thr Leu
1               5

<210> SEQ ID NO 11
<211> LENGTH: 17
<212> TYPE: PRT
<213> ORGANISM: Artificial Sequence
<220> FEATURE:
<223> OTHER INFORMATION: NES motif
```

-continued

```
<400> SEQUENCE: 11

Ala Cys Pro Val Pro Leu Gln Leu Pro Leu Glu Arg Leu Thr Leu
1               5                   10                  15

Asp

<210> SEQ ID NO 12
<211> LENGTH: 471
<212> TYPE: PRT
<213> ORGANISM: Artificial Sequence
<220> FEATURE:
<223> OTHER INFORMATION: fusion of NES and Methanosarcina mazei PylRS
      mutant
<220> FEATURE:
<221> NAME/KEY: SIGNAL
<222> LOCATION: 2..18
<223> OTHER INFORMATION: NES

<400> SEQUENCE: 12

Met Ala Cys Pro Val Pro Leu Gln Leu Pro Leu Glu Arg Leu Thr
1               5                   10                  15

Leu Asp Asp Lys Lys Pro Leu Asn Thr Leu Ile Ser Ala Thr Gly Leu
                20                  25                  30

Trp Met Ser Arg Thr Gly Thr Ile His Lys Ile Lys His His Glu Val
            35                  40                  45

Ser Arg Ser Lys Ile Tyr Ile Glu Met Ala Cys Gly Asp His Leu Val
        50                  55                  60

Val Asn Asn Ser Arg Ser Ser Arg Thr Ala Arg Ala Leu Arg His His
65                  70                  75                  80

Lys Tyr Arg Lys Thr Cys Lys Arg Cys Arg Val Ser Asp Glu Asp Leu
                85                  90                  95

Asn Lys Phe Leu Thr Lys Ala Asn Glu Asp Gln Thr Ser Val Lys Val
                100                 105                 110

Lys Val Val Ser Ala Pro Thr Arg Thr Lys Lys Ala Met Pro Lys Ser
            115                 120                 125

Val Ala Arg Ala Pro Lys Pro Leu Glu Asn Thr Glu Ala Ala Gln Ala
        130                 135                 140

Gln Pro Ser Gly Ser Lys Phe Ser Pro Ala Ile Pro Val Ser Thr Gln
145                 150                 155                 160

Glu Ser Val Ser Val Pro Ala Ser Val Ser Thr Ser Ile Ser Ser Ile
                165                 170                 175

Ser Thr Gly Ala Thr Ala Ser Ala Leu Val Lys Gly Asn Thr Asn Pro
            180                 185                 190

Ile Thr Ser Met Ser Ala Pro Val Gln Ala Ser Ala Pro Ala Leu Thr
        195                 200                 205

Lys Ser Gln Thr Asp Arg Leu Glu Val Leu Leu Asn Pro Lys Asp Glu
    210                 215                 220

Ile Ser Leu Asn Ser Gly Lys Pro Phe Arg Glu Leu Glu Ser Glu Leu
225                 230                 235                 240

Leu Ser Arg Arg Lys Lys Asp Leu Gln Gln Ile Tyr Ala Glu Glu Arg
                245                 250                 255

Glu Asn Tyr Leu Gly Lys Leu Glu Arg Glu Ile Thr Arg Phe Phe Val
            260                 265                 270

Asp Arg Gly Phe Leu Glu Ile Lys Ser Pro Ile Leu Ile Pro Leu Glu
        275                 280                 285

Tyr Ile Glu Arg Met Gly Ile Asp Asn Asp Thr Glu Leu Ser Lys Gln
    290                 295                 300
```

```
Ile Phe Arg Val Asp Lys Asn Phe Cys Leu Arg Pro Met Leu Ala Pro
305                 310                 315                 320

Asn Leu Ala Asn Tyr Leu Arg Lys Leu Asp Arg Ala Leu Pro Asp Pro
            325                 330                 335

Ile Lys Ile Phe Glu Ile Gly Pro Cys Tyr Arg Lys Glu Ser Asp Gly
            340                 345                 350

Lys Glu His Leu Glu Glu Phe Thr Met Leu Asn Phe Cys Gln Met Gly
        355                 360                 365

Ser Gly Cys Thr Arg Glu Asn Leu Glu Ser Ile Ile Thr Asp Phe Leu
370                 375                 380

Asn His Leu Gly Ile Asp Phe Lys Ile Val Gly Asp Ser Cys Met Val
385                 390                 395                 400

Phe Gly Asp Thr Leu Asp Val Met His Gly Asp Leu Glu Leu Ser Ser
                405                 410                 415

Ala Val Val Gly Pro Ile Pro Leu Asp Arg Glu Trp Gly Ile Asp Lys
            420                 425                 430

Pro Trp Ile Gly Ala Gly Phe Gly Leu Glu Arg Leu Leu Lys Val Lys
            435                 440                 445

His Asp Phe Lys Asn Ile Lys Arg Ala Ala Arg Ser Glu Ser Tyr Tyr
        450                 455                 460

Asn Gly Ile Ser Thr Asn Leu
465                 470

<210> SEQ ID NO 13
<211> LENGTH: 471
<212> TYPE: PRT
<213> ORGANISM: Artificial Sequence
<220> FEATURE:
<223> OTHER INFORMATION: fusion of Methanosarcina mazei PylRS mutant and
      NES
<220> FEATURE:
<221> NAME/KEY: SIGNAL
<222> LOCATION: 455..471
<223> OTHER INFORMATION: NES

<400> SEQUENCE: 13

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160
```

```
Thr Gly Ala Thr Ala Ser Ala Leu Val Lys Gly Asn Thr Asn Pro Ile
            165                 170                 175
Thr Ser Met Ser Ala Pro Val Gln Ala Ser Pro Ala Leu Thr Lys
        180                 185                 190
Ser Gln Thr Asp Arg Leu Glu Val Leu Leu Asn Pro Lys Asp Glu Ile
        195                 200                 205
Ser Leu Asn Ser Gly Lys Pro Phe Arg Glu Leu Glu Ser Glu Leu Leu
    210                 215                 220
Ser Arg Arg Lys Lys Asp Leu Gln Gln Ile Tyr Ala Glu Glu Arg Glu
225                 230                 235                 240
Asn Tyr Leu Gly Lys Leu Glu Arg Glu Ile Thr Arg Phe Phe Val Asp
                245                 250                 255
Arg Gly Phe Leu Glu Ile Lys Ser Pro Ile Leu Ile Pro Leu Glu Tyr
                260                 265                 270
Ile Glu Arg Met Gly Ile Asp Asn Asp Thr Glu Leu Ser Lys Gln Ile
            275                 280                 285
Phe Arg Val Asp Lys Asn Phe Cys Leu Arg Pro Met Leu Ala Pro Asn
        290                 295                 300
Leu Ala Asn Tyr Leu Arg Lys Leu Asp Arg Ala Leu Pro Asp Pro Ile
305                 310                 315                 320
Lys Ile Phe Glu Ile Gly Pro Cys Tyr Arg Lys Glu Ser Asp Gly Lys
                325                 330                 335
Glu His Leu Glu Glu Phe Thr Met Leu Asn Phe Cys Gln Met Gly Ser
            340                 345                 350
Gly Cys Thr Arg Glu Asn Leu Glu Ser Ile Ile Thr Asp Phe Leu Asn
        355                 360                 365
His Leu Gly Ile Asp Phe Lys Ile Val Gly Asp Ser Cys Met Val Phe
    370                 375                 380
Gly Asp Thr Leu Asp Val Met His Gly Asp Leu Glu Leu Ser Ser Ala
385                 390                 395                 400
Val Val Gly Pro Ile Pro Leu Asp Arg Glu Trp Gly Ile Asp Lys Pro
                405                 410                 415
Trp Ile Gly Ala Gly Phe Gly Leu Glu Arg Leu Leu Lys Val Lys His
            420                 425                 430
Asp Phe Lys Asn Ile Lys Arg Ala Ala Arg Ser Glu Ser Tyr Tyr Asn
        435                 440                 445
Gly Ile Ser Thr Asn Leu Ala Cys Pro Val Pro Leu Gln Leu Pro Pro
    450                 455                 460
Leu Glu Arg Leu Thr Leu Asp
465                 470

<210> SEQ ID NO 14
<211> LENGTH: 471
<212> TYPE: PRT
<213> ORGANISM: Artificial Sequence
<220> FEATURE:
<223> OTHER INFORMATION: fusion of NES and Methanosarcina mazei PylRS
<220> FEATURE:
<221> NAME/KEY: SIGNAL
<222> LOCATION: 2..18
<223> OTHER INFORMATION: NES

<400> SEQUENCE: 14

Met Ala Cys Pro Val Pro Leu Gln Leu Pro Pro Leu Glu Arg Leu Thr
1               5                   10                  15
Leu Asp Asp Lys Lys Pro Leu Asn Thr Leu Ile Ser Ala Thr Gly Leu
            20                  25                  30
```

-continued

```
Trp Met Ser Arg Thr Gly Thr Ile His Lys Ile Lys His His Glu Val
        35                  40                  45
Ser Arg Ser Lys Ile Tyr Ile Glu Met Ala Cys Gly Asp His Leu Val
    50                  55                  60
Val Asn Asn Ser Arg Ser Ser Arg Thr Ala Arg Ala Leu Arg His His
 65                  70                  75                  80
Lys Tyr Arg Lys Thr Cys Lys Arg Cys Arg Val Ser Asp Glu Asp Leu
                85                  90                  95
Asn Lys Phe Leu Thr Lys Ala Asn Glu Asp Gln Thr Ser Val Lys Val
            100                 105                 110
Lys Val Val Ser Ala Pro Thr Arg Thr Lys Lys Ala Met Pro Lys Ser
        115                 120                 125
Val Ala Arg Ala Pro Lys Pro Leu Glu Asn Thr Glu Ala Ala Gln Ala
    130                 135                 140
Gln Pro Ser Gly Ser Lys Phe Ser Pro Ala Ile Pro Val Ser Thr Gln
145                 150                 155                 160
Glu Ser Val Ser Val Pro Ala Ser Val Ser Thr Ser Ile Ser Ser Ile
                165                 170                 175
Ser Thr Gly Ala Thr Ala Ser Ala Leu Val Lys Gly Asn Thr Asn Pro
            180                 185                 190
Ile Thr Ser Met Ser Ala Pro Val Gln Ala Ser Ala Pro Ala Leu Thr
        195                 200                 205
Lys Ser Gln Thr Asp Arg Leu Glu Val Leu Leu Asn Pro Lys Asp Glu
    210                 215                 220
Ile Ser Leu Asn Ser Gly Lys Pro Phe Arg Glu Leu Glu Ser Glu Leu
225                 230                 235                 240
Leu Ser Arg Arg Lys Lys Asp Leu Gln Gln Ile Tyr Ala Glu Glu Arg
                245                 250                 255
Glu Asn Tyr Leu Gly Lys Leu Glu Arg Glu Ile Thr Arg Phe Phe Val
            260                 265                 270
Asp Arg Gly Phe Leu Glu Ile Lys Ser Pro Ile Leu Ile Pro Leu Glu
        275                 280                 285
Tyr Ile Glu Arg Met Gly Ile Asp Asn Asp Thr Glu Leu Ser Lys Gln
    290                 295                 300
Ile Phe Arg Val Asp Lys Asn Phe Cys Leu Arg Pro Met Leu Ala Pro
305                 310                 315                 320
Asn Leu Tyr Asn Tyr Leu Arg Lys Leu Asp Arg Ala Leu Pro Asp Pro
                325                 330                 335
Ile Lys Ile Phe Glu Ile Gly Pro Cys Tyr Arg Lys Glu Ser Asp Gly
            340                 345                 350
Lys Glu His Leu Glu Glu Phe Thr Met Leu Asn Phe Cys Gln Met Gly
        355                 360                 365
Ser Gly Cys Thr Arg Glu Asn Leu Glu Ser Ile Ile Thr Asp Phe Leu
    370                 375                 380
Asn His Leu Gly Ile Asp Phe Lys Ile Val Gly Asp Ser Cys Met Val
385                 390                 395                 400
Tyr Gly Asp Thr Leu Asp Val Met His Gly Asp Leu Glu Leu Ser Ser
                405                 410                 415
Ala Val Val Gly Pro Ile Pro Leu Asp Arg Glu Trp Gly Ile Asp Lys
            420                 425                 430
Pro Trp Ile Gly Ala Gly Phe Gly Leu Glu Arg Leu Leu Lys Val Lys
        435                 440                 445
```

His Asp Phe Lys Asn Ile Lys Arg Ala Ala Arg Ser Glu Ser Tyr Tyr
            450                 455                 460

Asn Gly Ile Ser Thr Asn Leu
465                 470

<210> SEQ ID NO 15
<211> LENGTH: 471
<212> TYPE: PRT
<213> ORGANISM: Artificial Sequence
<220> FEATURE:
<223> OTHER INFORMATION: fusion of Methanosarcina mazei PylRS and NES
<220> FEATURE:
<221> NAME/KEY: SIGNAL
<222> LOCATION: 455..471
<223> OTHER INFORMATION: NES

<400> SEQUENCE: 15

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
            355                 360                 365

His Leu Gly Ile Asp Phe Lys Ile Val Gly Asp Ser Cys Met Val Tyr
        370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu Ala Cys Pro Val Pro Leu Gln Leu Pro Pro
        450                 455                 460

Leu Glu Arg Leu Thr Leu Asp
465                 470

<210> SEQ ID NO 16
<211> LENGTH: 436
<212> TYPE: PRT
<213> ORGANISM: Artificial Sequence
<220> FEATURE:
<223> OTHER INFORMATION: fusion of NES and Methanosarcina barkeri PylRS
<220> FEATURE:
<221> NAME/KEY: SIGNAL
<222> LOCATION: 2..18
<223> OTHER INFORMATION: NES

<400> SEQUENCE: 16

Met Ala Cys Pro Val Pro Leu Gln Leu Pro Leu Glu Arg Leu Thr
1               5                   10                  15

Leu Asp Asp Lys Lys Pro Leu Asp Val Leu Ile Ser Ala Thr Gly Leu
            20                  25                  30

Trp Met Ser Arg Thr Gly Thr Leu His Lys Ile Lys His His Glu Val
        35                  40                  45

Ser Arg Ser Lys Ile Tyr Ile Glu Met Ala Cys Gly Asp His Leu Val
    50                  55                  60

Val Asn Asn Ser Arg Ser Cys Arg Thr Ala Arg Ala Phe Arg His His
65                  70                  75                  80

Lys Tyr Arg Lys Thr Cys Lys Arg Cys Arg Val Ser Asp Glu Asp Ile
                85                  90                  95

Asn Asn Phe Leu Thr Arg Ser Thr Glu Ser Lys Asn Ser Val Lys Val
            100                 105                 110

Arg Val Val Ser Ala Pro Lys Val Lys Lys Ala Met Pro Lys Ser Val
        115                 120                 125

Ser Arg Ala Pro Lys Pro Leu Glu Asn Ser Val Ser Ala Lys Ala Ser
    130                 135                 140

Thr Asn Thr Ser Arg Ser Val Pro Ser Pro Ala Lys Ser Thr Pro Asn
145                 150                 155                 160

Ser Ser Val Pro Ala Ser Ala Pro Ala Pro Ser Leu Thr Arg Ser Gln
                165                 170                 175

Leu Asp Arg Val Glu Ala Leu Leu Ser Pro Glu Asp Lys Ile Ser Leu

```
            180                 185                 190
Asn Met Ala Lys Pro Phe Arg Glu Leu Glu Pro Glu Leu Val Thr Arg
        195                 200                 205

Arg Lys Asn Asp Phe Gln Arg Leu Tyr Thr Asn Asp Arg Glu Asp Tyr
    210                 215                 220

Leu Gly Lys Leu Glu Arg Asp Ile Thr Lys Phe Val Asp Arg Gly
225                 230                 235                 240

Phe Leu Glu Ile Lys Ser Pro Ile Leu Ile Pro Ala Glu Tyr Val Glu
                245                 250                 255

Arg Met Gly Ile Asn Asn Asp Thr Glu Leu Ser Lys Gln Ile Phe Arg
            260                 265                 270

Val Asp Lys Asn Leu Cys Leu Arg Pro Met Leu Ala Pro Thr Leu Tyr
        275                 280                 285

Asn Tyr Leu Arg Lys Leu Asp Arg Ile Leu Pro Gly Pro Ile Lys Ile
    290                 295                 300

Phe Glu Val Gly Pro Cys Tyr Arg Lys Glu Ser Asp Gly Lys Glu His
305                 310                 315                 320

Leu Glu Glu Phe Thr Met Val Asn Phe Cys Gln Met Gly Ser Gly Cys
                325                 330                 335

Thr Arg Glu Asn Leu Glu Ala Leu Ile Lys Glu Phe Leu Asp Tyr Leu
            340                 345                 350

Glu Ile Asp Phe Glu Ile Val Gly Asp Ser Cys Met Val Tyr Gly Asp
        355                 360                 365

Thr Leu Asp Ile Met His Gly Asp Leu Glu Leu Ser Ser Ala Val Val
    370                 375                 380

Gly Pro Val Ser Leu Asp Arg Glu Trp Gly Ile Asp Lys Pro Trp Ile
385                 390                 395                 400

Gly Ala Gly Phe Gly Leu Glu Arg Leu Leu Lys Val Met His Gly Phe
                405                 410                 415

Lys Asn Ile Lys Arg Ala Ser Arg Ser Glu Ser Tyr Tyr Asn Gly Ile
            420                 425                 430

Ser Thr Asn Leu
        435

<210> SEQ ID NO 17
<211> LENGTH: 436
<212> TYPE: PRT
<213> ORGANISM: Artificial Sequence
<220> FEATURE:
<223> OTHER INFORMATION: fusion of Methanosarcina barkeri PylRS and NES
<220> FEATURE:
<221> NAME/KEY: SIGNAL
<222> LOCATION: 420..436
<223> OTHER INFORMATION: NES

<400> SEQUENCE: 17

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80
```

Asn Phe Leu Thr Arg Ser Thr Glu Ser Lys Asn Ser Val Lys Val Arg
                 85                  90                  95

Val Val Ser Ala Pro Lys Val Lys Ala Met Pro Lys Ser Val Ser
            100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
                180                 185                 190

Lys Asn Asp Phe Gln Arg Leu Tyr Thr Asn Asp Arg Glu Asp Tyr Leu
                195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
                260                 265                 270

Tyr Leu Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
        290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu Ala Cys Pro Val Pro Leu Gln Leu Pro Pro Leu Glu Arg
            420                 425                 430

Leu Thr Leu Asp
        435

<210> SEQ ID NO 18
<211> LENGTH: 36
<212> TYPE: DNA
<213> ORGANISM: Artificial Sequence
<220> FEATURE:
<223> OTHER INFORMATION: digoxigenin-labeled hybridization probe
<220> FEATURE:
<221> NAME/KEY: misc_difference
<222> LOCATION: 1

```
<223> OTHER INFORMATION: /note="5' coupled to digoxigenin"

<400> SEQUENCE: 18
ctaacccggc tgaacggatt tagagtccat tcgatc                              36

<210> SEQ ID NO 19
<211> LENGTH: 11
<212> TYPE: DNA
<213> ORGANISM: Artificial Sequence
<220> FEATURE:
<223> OTHER INFORMATION: tetrazine-coupled docking strand
      oligonucleotide
<220> FEATURE:
<221> NAME/KEY: misc_difference
<222> LOCATION: 1
<223> OTHER INFORMATION: /note="5' coupled to 1,2,4,5-tetrazine"

<400> SEQUENCE: 19
ttatacatct a                                                         11

<210> SEQ ID NO 20
<211> LENGTH: 10
<212> TYPE: DNA
<213> ORGANISM: Artificial Sequence
<220> FEATURE:
<223> OTHER INFORMATION: Atto655-coupled imager strand
<220> FEATURE:
<221> NAME/KEY: misc_difference
<222> LOCATION: 10
<223> OTHER INFORMATION: /note="3' coupled to Atto655"

<400> SEQUENCE: 20
ctagatgtat                                                           10
```